United States Patent
Shen et al.

(10) Patent No.: US 11,186,864 B2
(45) Date of Patent: *Nov. 30, 2021

(54) **NICKING AND EXTENSION AMPLIFICATION REACTION (NEAR) OF *STREPTOCOCCUS* SPECIES**

(71) Applicant: Ionian Technologies, LLC, San Diego, CA (US)

(72) Inventors: Daiwei Shen, San Diego, CA (US); Richard Roth, Carlsbad, CA (US); Honghua Zhang, San Diego, CA (US)

(73) Assignee: IONIAN TECHNOLOGIES, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/417,071

(22) Filed: May 20, 2019

(65) Prior Publication Data

US 2019/0338347 A1 Nov. 7, 2019

Related U.S. Application Data

(63) Continuation of application No. 15/391,002, filed on Dec. 27, 2016, now Pat. No. 10,329,601.

(60) Provisional application No. 62/271,400, filed on Dec. 28, 2015.

(51) Int. Cl.
*C12Q 1/6844* (2018.01)

(52) U.S. Cl.
CPC ..... *C12Q 1/6844* (2013.01); *C12Q 2600/158* (2013.01)

(58) Field of Classification Search
CPC .................................................. C12Q 1/6844
See application file for complete search history.

(56) References Cited

U.S. PATENT DOCUMENTS

| | | | |
|---|---|---|---|
| 6,130,038 A | 10/2000 | Becker et al. | |
| 7,270,981 B2 | 9/2007 | Armes et al. | |
| 7,399,590 B2 | 7/2008 | Piepenburg et al. | |
| 7,435,561 B2 | 10/2008 | Piepenburg et al. | |
| 7,666,598 B2 | 2/2010 | Piepenburg et al. | |
| 9,096,897 B2 | 8/2015 | Shaffer et al. | |
| 10,329,601 B2* | 6/2019 | Shen | C12Q 1/6844 |
| 2003/0211483 A1 | 11/2003 | Schroeder et al. | |
| 2006/0194751 A1* | 8/2006 | Meinke | A61P 31/04 514/44 R |
| 2007/0117113 A1* | 5/2007 | Farnet | C12N 15/52 435/6.16 |
| 2009/0017453 A1* | 1/2009 | Maples | C12Q 1/686 435/6.12 |
| 2009/0029421 A1 | 1/2009 | Piepenburg et al. | |
| 2009/0081670 A1 | 3/2009 | Maples et al. | |
| 2010/0136041 A1* | 6/2010 | Grandi | C07K 14/315 424/190.1 |
| 2010/0166732 A1* | 7/2010 | Meinke | C07K 14/315 424/130.1 |
| 2011/0038879 A1* | 2/2011 | Scarselli | A61P 37/04 424/165.1 |
| 2013/0330777 A1* | 12/2013 | Zhang | C12P 19/34 435/91.2 |
| 2015/0132337 A1* | 5/2015 | Grandi | A61P 37/04 424/190.1 |
| 2017/0183714 A1 | 6/2017 | Shen et al. | |

FOREIGN PATENT DOCUMENTS

WO    WO2010/141940    12/2010

OTHER PUBLICATIONS

Cohen DM, Russo ME, Jaggi P, Kline J, Gluckman W, Parekh A. Multicenter Clinical Evaluation of the Novel Alere i Strep A Isothermal Nucleic Acid Amplification Test. J Clin Microbiol. Jul. 2015; 53(7):2258-61. Epub May 13, 2015. (Year: 2015).*
Genbank Accession No. EU730695—*Streptococcus pyogenes* strain H342 cell envelope proteinase (cepA) gene, complete cds (submitted on May 20, 2008 Jun. 7, 2010, retrieved on Sep. 27, 2020 from http://www.ncbi.nlm.nih.gov/nuccore/EU730695) (Year: 2008).*
Timmer. Virulence mechanisms of Group A *streptococcus*. UCSD. Ph. Dissertation published Jan. 1, 2008. (Year: 2008).*
Roth R., Rapid Isothermal Nucleic Acid Assays for the Detection of Pathogens, Lab Automation 2008, presentation dated Jan. 2007, 22 pages. (Year: 2008).*
Cohen et al., "Multicenter Clinical Evaluation of the Novel Alere i Strep A Isothermal Nucleic Acid Amplification Test." J Clin Microbiol. Jul. 2015;53(7):2258-61.
Genbank Accession No. EU730695—*Streptococcus pyogenes* strain H342 cell envelope proteinase (cepA) gene, complete cds (submitted on May 20, 2008 Jun. 7, 2010, retrieved on Jun. 25, 2018 from http://www.ncbi.nlm.nih.gov/nuccore/EU730695). (Year:2008).
Hoopes et a., "Use of a bacteriophage lysin, PlyC, as an enzyme disinfectant against *Streptococcus equi*." Appl Environ Microbiol. Mar. 2009;75(5):1388-94.
http:/www.alere.com/ww/en/product-details/alere-i-strep-a.html, downloaded Oct. 30, 2017, pp. 1-11.

* cited by examiner

*Primary Examiner* — Teresa E Strzelecka
*Assistant Examiner* — Olayinka A Oyeyemi
(74) *Attorney, Agent, or Firm* — Casimir Jones, S.C.; Thomas A. Isenbarger

(57) ABSTRACT

This invention relates to compositions, methods and kits for detecting the presence or absence of a bacterial species in a biological sample using isothermal nucleic acid amplification.

25 Claims, 10 Drawing Sheets
Specification includes a Sequence Listing.

NICKING AND EXTENSION AMPLIFICATION REACTION (NEAR) OF *STREPTOCOCCUS* SPECIES

CLAIM OF PRIORITY

This application is a continuation of U.S. application Ser. No. 15/391,002, filed Dec. 27, 2016, now U.S. Pat. No. 10,329,601, issued Jun. 25, 2019, which claims the benefit of U.S. Provisional Patent Application Ser. No. 62/271,400, filed on Dec. 28, 2015; the entire contents of which are hereby incorporated by reference.

TECHNICAL FIELD

This invention relates to methods and compositions for detecting the presence or absence of a bacterial species in a biological sample using isothermal nucleic acid amplification. More specifically, the present invention relates to using Nicking and Extension Amplification Reaction (NEAR) to detect *Streptococcus pyogenes* (GAS or Strep A) in a biological sample.

BACKGROUND

Certain isothermal amplification methods are able to amplify a target nucleic acid from trace levels to very high and detectable levels within a matter of minutes. Such isothermal methods, e.g., Nicking and Extension Amplification Reaction (NEAR), allow users to detect a particular nucleotide sequence in trace amounts, facilitating point-of-care testing and increasing the accessibility and speed of diagnostics.

*Streptococcus pyogenes* is the causative agent of group A streptococcal (GAS) infections such as pharyngitis, impetigo, and life-threatening necrotizing fasciitis and sepsis. The most common GAS infection, pharyngitis, can be diagnosed by collecting a throat swab sample from a patient and culturing the sample under conditions that would enable bacterial, specifically *S. pyogenes*, growth, which takes 2-3 days. Culturing *S. pyogenes* is an accurate and reliable method of diagnosing GAS, but it is slow. A 2-3 day delay in prescribing appropriate antibiotic treatment can result in unnecessary patient suffering and potentially the onset of life threatening conditions such as rheumatic fever. In the recent past, biochemical methods have been developed to detect *S. pyogenes*, but these methods do not provide the necessary characteristics to be deployed in the point-of-care setting, either due to a lack of sensitivity or time to result (speed).

Accordingly, a highly sensitive and rapid qualitative assay for the detection and diagnosis of a *S. pyogenes* infection is desired.

SUMMARY

This disclosure is based, at least in part, on the discovery that the presence or absence of *S. pyogenes* (GAS or Strep A) in a biological sample can be accurately and efficiently detected in using the Nicking and Extension Amplification Reaction (NEAR). In view of this discovery, provided herein are NEAR compositions and methods for detecting the presence or absence of a *S. pyogenes* in a biological sample. The compositions provided herein are useful for the detection of *S. pyogenes* nucleic acid in a biological sample, and comprise at least one pair of templates (i.e., a forward and reverse template pair), and optionally a probe, specific for *S. pyogenes*.

In one aspect, this disclosure features compositions that include a forward template comprising a nucleic acid sequence comprising a recognition region at the 3' end that is complementary to the 3' end of the *S. pyogenes* target nucleic acid sequence, a nicking enzyme binding site and a nicking site upstream of said recognition region, and a stabilizing region upstream of said nicking site; and a reverse template comprising a nucleotide sequence comprising a recognition region at the 3' end that is complementary to the 3' end of the *S. pyogenes* target nucleic acid sequence, a nicking enzyme binding site and a nicking site upstream of said recognition region, and, a stabilizing region upstream of said nicking site. The portion of the template that is complementary to the target nucleotide sequence can be 8-30 nucleotides in length, 8-25 nucleotides in length, 8-20 nucleotides in length, or 8-15 nucleotides in length.

In some embodiments, *S. pyogenes* target nucleic acid sequence is found within the *S. pyogenes* cell envelope proteinase A (cepA) gene sequence. Accordingly, the forward template comprises a recognition region at the 3' end that is complementary to the 3' end of the *S. pyogenes* cepA gene antisense strand, and the reverse template comprises a recognition region at the 3' end that is complementary to the 3' end of the *S. pyogenes* cepA gene sense strand. Accordingly, the portion of the recognition region that is complementary to the 3' end of the target antisense strand is 8-30 nucleotides in length and the recognition region that is complementary to the 3' end of the target sense strand is 8-30 nucleotides in length.

In some embodiments, the compositions disclosed herein further comprise an oligonucleotide probe comprising a sequence complementary to the *S. pyogenes* target nucleotide sequence (e.g., the *S. pyogenes* cepA nucleotide sequence). In some embodiments of all aspects, the composition includes a probe labeled with a detectable label. In some embodiments, the detectable label is a fluorophore, an enzyme, a quencher, an enzyme inhibitor, a radioactive label, an electrochemical label, a chemiluminescent label, a metal particle, a latex particle, one member of a binding pair or any combination thereof.

In some embodiments of any of the aspects described here, the target nucleic acid sequence is also combined with a probe labeled with a detectable label. In some embodiments of all aspects, the probe comprises an oligonucleotide complimentary to a portion of the target nucleic acid sequence at a position that is in between the portions of the target nucleic acid sequence that are complementary to the first and the second templates.

In some embodiments, the portion of the nucleic acid sequence that is complementary to the 3' end of the target antisense strand is 8-30 nucleotides in length.

This disclosure also provides methods for detecting the presence or absence of *S. pyogenes* in a biological sample by identifying *S. pyogenes* nucleic acid in the sample. In some aspects, this disclosure features methods for the detection of the presence or absence of *S. pyogenes* in a biological sample, the methods comprising contacting the biological sample with components of a nucleic amplification reaction for a *S. pyogenes* target nucleic acid sequence comprising i) a forward template comprising a nucleic acid sequence comprising a recognition region at the 3' end that is complementary to the 3' end of the *S. pyogenes* target nucleic acid sequence; a nicking enzyme binding site and a nicking site upstream of said recognition region, and a stabilizing region upstream of said nicking site, ii) a reverse template comprising a nucleotide sequence comprising a recognition region at the 3' end that is complementary to the 3' end of the S. pyogenes target nucleic acid sequence; a nicking enzyme binding site and a nicking site upstream of said recognition region, and, a stabilizing region upstream of said nicking site, (iii) a first nicking enzyme that is capable of nicking at the nicking site of said forward template, and does not nick within said target sequence, (iv) a second nicking enzyme that is capable of nicking at the nicking site of said reverse template and does not nick within said target sequence, and (v) a DNA polymerase; amplifying the target nucleic acid sequence in a nucleic amplification reaction to provide an amplification product; and determining (e.g., detecting) the presence or absence of the amplification product.

According to any embodiment of the methods provided herein, amplification is performed by multiple cycles of said polymerase extending said forward and reverse templates along said target sequence producing a double-stranded nicking site, said nicking enzymes nicking at said nicking sites, and, following a first round of amplification, at amplified copies of said sites, producing an amplification product, thereby providing a product. In some embodiments, amplifying the target nucleic acid sequence comprises performing an isothermal nucleic amplification reaction. Such isothermal methods, include NEAR and Recombinase Polymerase Amplification (RPA) methods.

In some embodiments, the present amplification methods do not require the use of temperature cycling (i.e., the present amplification methods are performed isothermally), as often is required in methods of amplification to dissociate the target sequence from the amplified nucleic acid. The temperature of the reaction may vary based on the length of the sequence, and the GC concentration, but, as understood by those of ordinary skill in the art, the temperature should be high enough to minimize non-specific binding. The temperature should also be suitable for the enzymes of the reaction, the nicking enzyme and the polymerase. For example, the reaction may be run at about 52° C., 53° C., 54° C., 55° C., 56° C., 57° C., 58° C., 59° C., or 60° C. In some embodiments, the reaction is run at about 37° C.-85° C., 37° C.-60° C., 54° C.-60° C., 55° C.-60° C., 58° C.-60° C. and, in exemplary embodiments, from 56° C.-58° C. In certain embodiments, there is no denaturation step in the process. The entire amplification process, including interacting templates with target nucleic acid, is conducted within substantially isothermal conditions, and without a denaturing step (e.g., no significant temperature increase (e.g., no increase in temperature to 90-110° C.)), in some embodiments of the present methods.

In some embodiments of all aspects, the nucleic acid amplification reaction is NEAR. In some embodiments of all aspects, the monitoring of the rate of increase of nucleic acid amplification products in the mixture is performed in real-time.

According to any embodiment of the methods provided herein, determining (e.g. detecting) is performed using real-time fluorescence detection.

In some embodiments of any of the aspects described here, the target nucleic acid is genomic DNA. In some embodiments of all aspects, the target nucleic acid is double-stranded or single-stranded nucleic acid molecules, such as DNA (e.g., cDNA, gDNA, mtDNA, etc.) or RNA (e.g., vRNA, mRNA, snRNA, rRNA, tRNA, etc.).

In some embodiments, the S. pyogenes target nucleic acid sequence is found within the S. pyogenes cell envelope proteinase A (cepA) gene sequence. Thus, in some aspects, this disclosure features methods for the detection of the presence or absence of S. pyogenes in a biological sample, the methods comprising contacting a biological sample with components of a nucleic amplification reaction for a S. pyogenes target nucleic acid sequence comprising i) a forward template comprising a nucleic acid sequence comprising a recognition region at the 3' end that is complementary to the 3' end of the S. pyogenes cepA gene antisense strand; a nicking enzyme binding site and a nicking site upstream of said recognition region; and a stabilizing region upstream of said nicking site; ii) a reverse template comprising a nucleotide sequence comprising a recognition region at the 3' end that is complementary to the 3' end of the S. pyogenes cepA gene sense strand; a nicking enzyme binding site and a nicking site upstream of said recognition region; and a stabilizing region upstream of said nicking site; (iii) a first nicking enzyme that is capable of nicking at the nicking site of said forward template, and does not nick within said target sequence; (iv) a second nicking enzyme that is capable of nicking at the nicking site of said reverse template and does not nick within said target sequence; and (v) a DNA polymerase; amplifying the target nucleic acid sequence in a nucleic amplification reaction to provide an amplification product; and determining whether an indicator of the target nucleic acid species is present in the amplification product.

In some embodiments of all aspects, the components of a nucleic amplification reaction further comprise a probe oligonucleotide comprising a sequence complementary to the S. pyogenes cell envelope proteinase A (cepA) gene nucleotide sequence.

In some embodiment of all aspects, the nucleic amplification reaction is performed under essentially isothermal conditions.

The amplification may be, for example, conducted at a constant temperature. This temperature may be, for example, between 54° C. and 60° C. As to the length of time for the reaction to take place, in certain examples, the amplification reaction is held at constant temperature for 1 to 10 minutes.

In some embodiments of all aspects, the compositions disclosed herein comprise reagents suitable for NEAR amplification of a target sequence. In some embodiments of all aspects, the methods disclosed herein comprise combining a target nucleic acid with reagents suitable for NEAR amplification and performing NEAR amplification.

In some embodiments of the compositions and methods disclosed herein, specific probes and templates for detecting S. pyogenes are provided. Representative template sequences include a forward template comprising a nucleotide sequence having at least 80, 85 or 95% identity to SEQ ID NO: 1 (AGACTCCATATGGAGTCTAGCCAAACAGGAACA), and a reverse template comprising a nucleotide sequence having at least 80, 85 or 95% identity to SEQ ID NO: 2: (CGACTCCATATGGAGTCGAAAGCAATCTGAGGA); or a forward template comprising a nucleotide sequence having at least 80, 85, or 95% identity to SEQ ID NO: 8: (AGACTCCACACGGAGTCTAGCCAAACAGGAACA), and a reverse template comprising a nucleotide sequence having at least 80, 85, or 95% identity to SEQ ID NO: 9: (GGACTCCACACGGAGTCCGCCAGCAATCUGAGG). A representative probe oligonucleotide includes a nucleotide sequence having at least 80, 85 or 95% identity to SEQ ID NO: 3 (ACAAGTATGTGAGGAGAGGCCATACTTGT). In some embodiments of the compositions and methods described herein, the templates include a 3' or 5' modification.

In some embodiments of any of the aspects described here, the compositions disclosed herein further comprise one or more of a DNA polymerase, one or more nicking enzymes, dNTPs or a mixture of dNTPs and ddNTPs. The DNA polymerase can be selected from the group consisting of *Geobacillus bogazici* DNA polymerase, Bst (large fragment), exo-DNA Polymerase, Manta 1.0 DNA Polymerase (Enzymatics®).

The nicking enzyme may, for example, nick upstream of the nicking enzyme binding site, or, in exemplary embodiments, the nicking enzyme may nick downstream of the nicking enzyme binding site. In certain embodiments, the forward and reverse templates comprise nicking sites recognized by the same nicking enzyme and said first and said second nicking enzyme are the same. The nicking enzyme ("NE") may, for example, be selected from the group consisting of Nt.BspQI, Nb.BbvCi, Nb.BsmI, Nb.BsrDI, Nb.BtsI, Nt.AlwI, Nt.BbvCI, Nt.BstNBI, Nt.CviPII, Nb.Bpu10I, Nt.Bpu10I and N.BspD6I.

In some embodiments of any of the aspects described here, the composition further comprises a lytic agent, such as a bacteriophage lysin. In some embodiments the lytic agent is a bacteriophage lysin comprising streptococcal C1 bacteriophase lysin (PlyC).

In some embodiments of any of the aspects described here, the composition is a lyophilized composition.

In some embodiments of all aspects, the templates and/or probes can be labeled with (e.g., conjugated to) a detectable label. Representative detectable labels include a fluorophore, an enzyme, a quencher, an enzyme inhibitor, a radioactive label, a member of a binding pair, and combinations thereof. In some embodiments, the detectable label is a fluorescent moiety suitable for use in real-time nucleic amplification reactions. Such fluorescent moieties are known to persons skilled in the art and are available from various commercial sources.

In some embodiments of any of the aspects described here, the templates and/or probes can comprise comprises one or more modified nucleotides, spacers, or blocking groups. Representative modified nucleotides, spacers, or blocking groups include a 2' modification, a 2'-O-methyl, or at least one phosphorothioate. In some embodiments of any of the aspects described herein, the templates and/or probes can comprise a 2-Ome (2'-O-methyl) modification one or more (e.g., 1, 2, 3, 4, 5 or more) bases of the template and/or probe. For example, SEQ ID NO: 8 can include a 2'-O-methyl modification on five bases at the 3' end (AGACTC-CACACGGAGTCTAGCCAAACAGmGmAmCmA) or SEQ ID NO:9 can include a 2'-O-methyl modification on five bases at the 3' end (GGACTCCACACG-GAGTCCGCCAGCAATCmUmGmAmGmG).

In some aspects, the disclosure provides kits containing templates and probes for the detection of *S. pyogenes* in a biological sample and components of a nucleic acid amplification reaction, such as a polymerase. Representative template sequences include a forward template comprising a nucleotide sequence having at least 80, 85 or 95% identity to SEQ ID NO: 1 (AGACTCCATATGGAGTCTAGC-CAAACAGGAACA); a reverse template comprising a nucleotide sequence having at least 80, 85 or 95% identity to SEQ ID NO 2: (CGACTCCATATG-GAGTCGAAAGCAATCTGAGGA); and a probe oligonucleotide comprising a nucleotide sequence at least 80, 85 or 95% identity to SEQ ID NO: 3 (ACAAGTATGTGAG-GAGAGGCCATACTTGT). Representative template sequences also include a forward template comprising a nucleotide sequence having at least 80, 85 or 95% identity to SEQ ID NO: 8 (AGACTCCACACGGAGTCTAGC-CAAACAGGAACA); a reverse template comprising a nucleotide sequence having at least 80, 85 or 95% identity to SEQ ID NO: 9 (GGACTCCACACG-GAGTCCGCCAGCAATCUGAGG); and a probe oligonucleotide comprising a nucleotide sequence at least 80, 85 or 95% identity to SEQ ID NO: 3 (ACAAGTATGTGAG-GAGAGGCCATACTTGT).

In some embodiments, the kit contains instructions to use the kit. In some embodiments, the kits contain a swab for obtaining a biologic sample, dNTPs or a mixture of dNTPs and ddNTPs, and a lytic agent. In some embodiments, the kit comprises reagents for gaining access to and/or extracting/isolating nucleic acid from a biological sample.

The kit may, for example, provide said polymerase, nicking enzymes, and templates in a container. The kit may provide, for example, said polymerase, nicking enzymes, and templates in two containers. In certain examples, the polymerase and nicking enzymes are in a first container, and said templates are in a second container. In certain examples, the polymerase and nicking enzymes are lyophilized. The kit may, for example, further comprise instructions for following the amplification methods of the present invention. The kit may, for example, further comprise a lateral flow device or dipstick. The lateral flow device or dipstick may, for example, further comprise a capture probe, wherein said capture probe binds to the amplified product. The kit may, for example, further comprise a detector component, for example, one selected from the group consisting of a fluorescent dye, colloidal gold particles, latex particles, a molecular beacon, polystyrene beads, and the like. In other examples, at least one of the templates of the kit may comprise a spacer, blocking group, or modified nucleotides.

The term "template" or "primer" refers to an oligonucleotide that is capable of acting as a point of initiation for the 5' to 3' synthesis of a primer extension product that is complementary to a nucleic acid strand. The primer extension product is synthesized in the presence of appropriate nucleotides and an agent for polymerization, such as a DNA polymerase, in an appropriate buffer and at a suitable temperature.

As used herein, the term "probe" refers to an oligonucleotide that forms a hybrid structure with the product generated by amplification of the target nucleic acid sequence in a sample undergoing analysis, due to complementarity of at least one sequence in the probe with the target sequence. The nucleotides of any particular probe may be deoxyribonucleotides, ribonucleotides, and/or synthetic nucleotide analogs.

Within the context of the present invention, the target nucleic acid sequence is a nucleic acid sequence of *S. pyogenes*, i.e., GAS or Strep A.

The term "one or more" or "at least one" as used in the present invention stands for 1, 2, 3, 4, 5, 6, 7, 8, 9, 10 compound(s) or even more.

The terms "first" and "second" are used in this disclosure in their relative sense only. It will be understood that, unless otherwise noted, those terms are used merely as a matter of convenience in the description of one or more of the embodiments. The terms "first" and "second" are only used to distinguish one element from another element, and the scope of the rights of the disclosed technology should not be limited by these terms. For example, a first element may be designated as a second element, and similarly the second element may be designated as the first element.

The terms "increased", "increase" or "up-regulated" are all used herein to generally mean an increase by a statistically significant amount; for the avoidance of any doubt, the terms "increased" or "increase" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 0.5-fold, or at least about a 1.0-fold, or at least about a 1.2-fold, or at least about a 1.5-fold, or at least about a 2-fold, or at least about a 3-fold, or at least about a 4-fold, or at least about a 5-fold or at least about a 10-fold increase, or any increase between 1.0-fold and 10-fold or greater as compared to a reference level.

The terms "decrease", "decreased", "reduced", "reduction" or 'down-regulated" are all used herein generally to mean a decrease by a statistically significant amount. However, for avoidance of doubt, "reduced", "reduction", "decreased" or "decrease" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level, or at least about a 0.5-fold, or at least about a 1.0-fold, or at least about a 1.2-fold, or at least about a 1.5-fold, or at least about a 2-fold, or at least about a 3-fold, or at least about a 4-fold, or at least about a 5-fold or at least about a 10-fold decrease, or any decrease between 1.0-fold and 10-fold or greater as compared to a reference level.

The section headings used herein are for organizational purposes only and are not to be construed as limiting the described subject matter in any way. When definitions of terms in incorporated references appear to differ from the definitions provided in the present teachings, the definition provided in the present teachings shall control. It will be appreciated that there is an implied "about" prior to metrics such as temperatures, concentrations, and times discussed in the present teachings, such that slight and insubstantial deviations are within the scope of the present teachings herein. In this application, the use of the singular includes the plural unless specifically stated otherwise. Also, the use of "comprise," "comprises," "comprising," "contain," "contains," "containing," "include," "includes," and "including" are not intended to be limiting. It is to be understood that both the foregoing general description and the following detailed description are exemplary and explanatory only and are not restrictive of the invention. The articles "a" and "an" are used herein to refer to one or to more than one (i.e., to at least one) of the grammatical object of the article. By way of example, "an element" means one element or more than one element.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and are not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
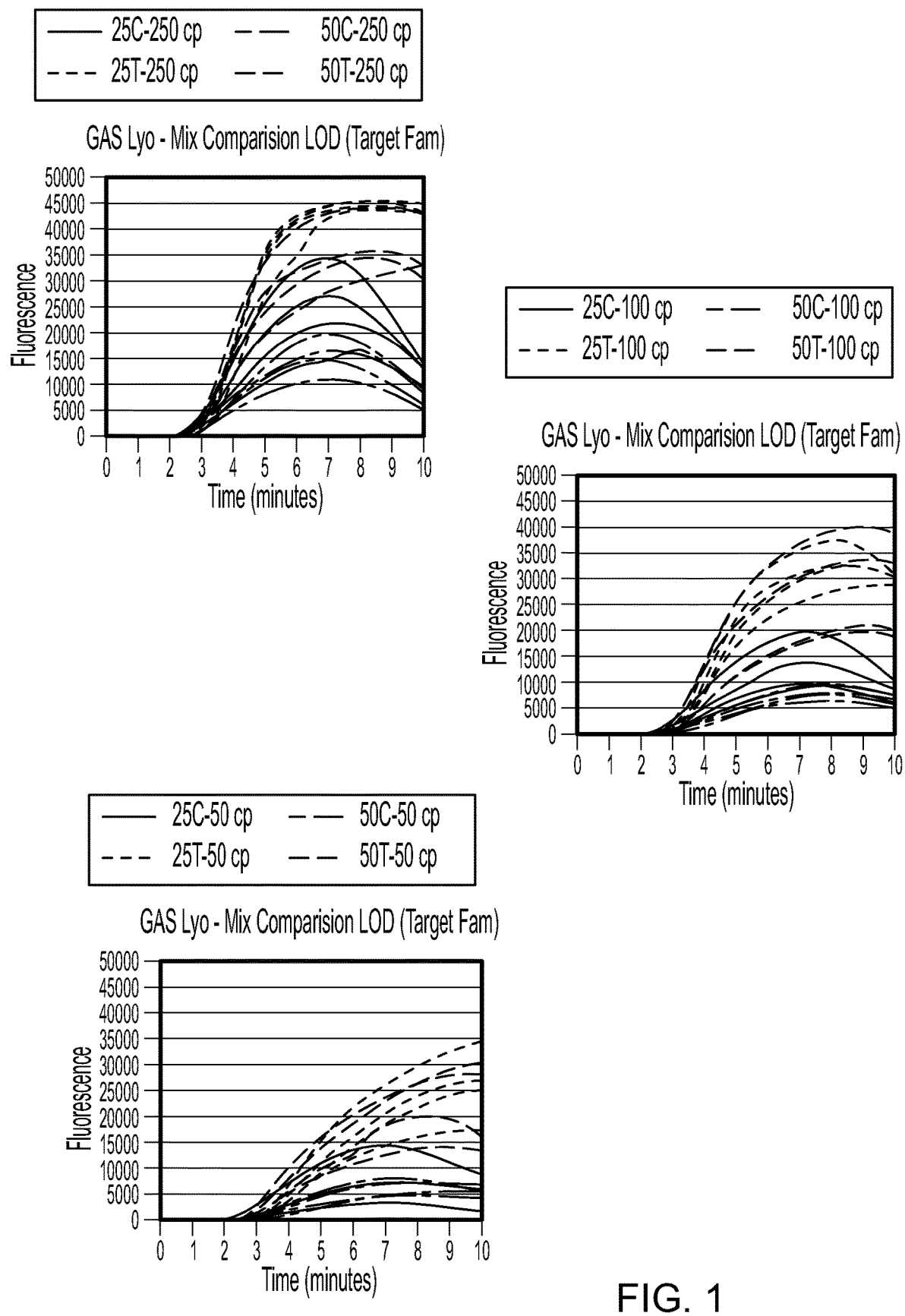
FIG. 1 shows the results of an exemplary limit of detection (LOD) study performed comparing four mixes containing the target assay (25C—complete assay, 4×25 µl lyo pellet; 25T—target only assay, 4×25 µl lyo pellet; 50C—complete assay, 2×50 µl lyo pellet; 50T—target only assay, 2×50 µl lyo pellet). Reactions were performed on the Stratagene Mx3005P thermal cycler using a standard 'hot start' approach.
Figure 1:
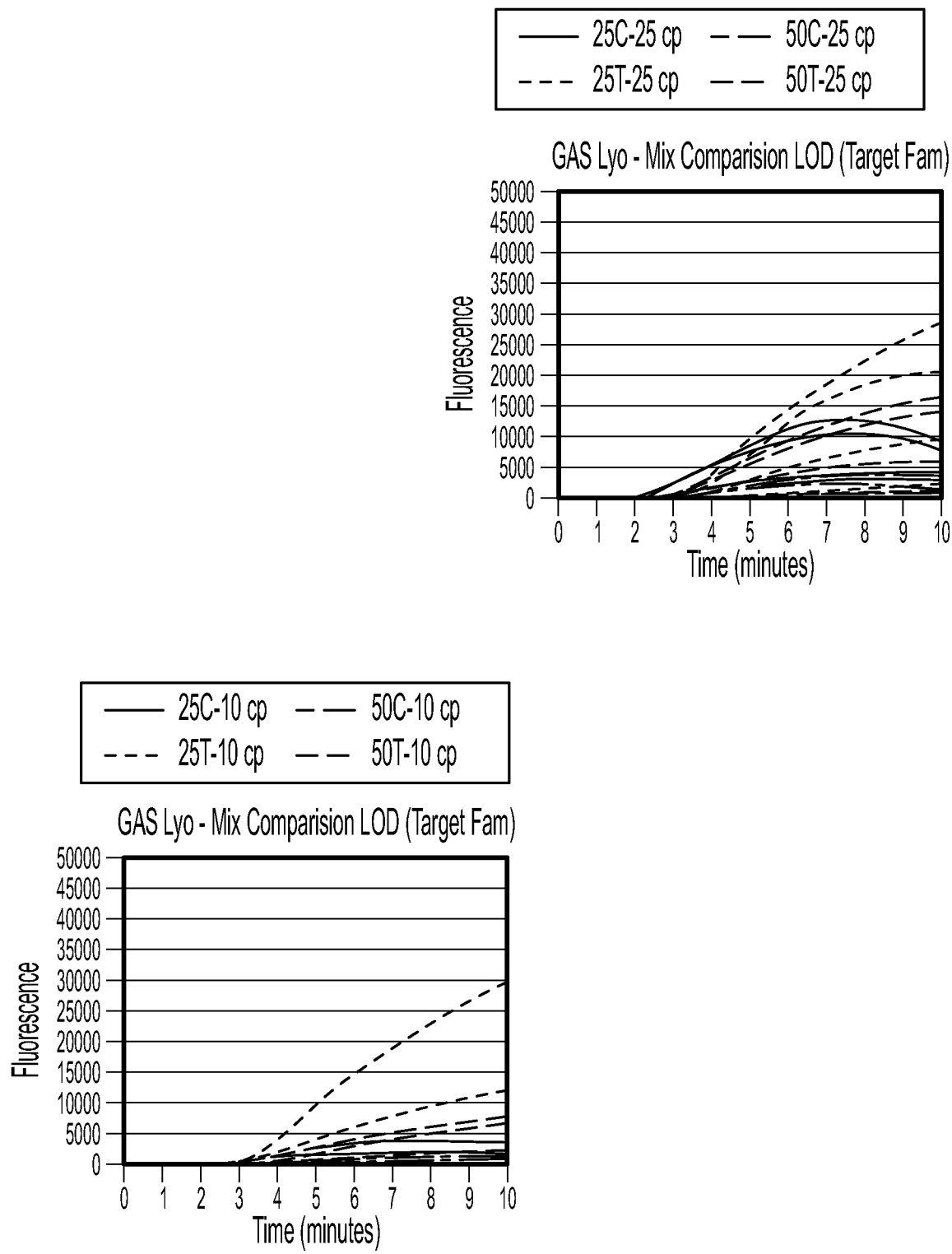

This disclosure is based in part on the discovery that it is possible to detect the presence or absence of S. pyogenes in a biological sample using isothermal amplification. To that end, the present application discloses a composition for detecting the presence or absence of S. pyogenes in a biological sample by amplifying and detecting a target nucleotide sequence using NEAR coupled with a real-time fluorescence (e.g., real-time PCR). In some embodiments, the target nucleotide sequence can be detected using real-time fluorescence approaches.

The use of the term "target sequence" may refer to either the sense or antisense strand of the sequence, and also refers to the sequences as they exist on target nucleic acids, amplified copies, or amplification products, of the original target sequence. The amplification product may be a larger molecule that comprises the target sequence, as well as at least one other sequence, or other nucleotides.

Methods of this invention can be used to identify nucleic acid from specimens for diagnosis of S. pyogenes infection. The specific primers and probes of the invention that are used in these methods allow for the amplification of and monitoring the development of specific amplification products. The increased sensitivity of NEAR for detection of S.

*pyogenes* as well as the improved features of real-time fluorescence including sample containment and real-time detection of the amplified product, make feasible the implementation of this technology for routine diagnosis of *S. pyogenes* infections in the clinical laboratory and at point-of-care.

Certain isothermal amplification methods are able to amplify target nucleic acid from trace levels to very high and detectable levels within a matter of minutes. Such isothermal methods, e.g., NEAR and RPA can allow users to detect a particular sequence in trace amounts, facilitating point-of-care testing and increasing the accessibility and speed of diagnostics.

The time that the amplification reaction is run may vary from, for example, within about 1 minute, or within about 2, 3, 4, 5, 6, 7, 8, 9, 10, 11, 12, 13, 14, 15, 16, 17, 18, 19 or 20 minutes. Longer reaction times may produce acceptable results where speed is not an issue. In some embodiments, the reaction is between 1-20 minutes, 1-15 minutes or 1-10, 1-8, 1-5, 1-2.5, 2.5-5, 2.5-8, 2.5-10, or 2.5-20 minutes in certain embodiments. The amplification processes described herein are efficient, and in some embodiments, there is about $1 \times 10^6$-fold, or more amplification, about $1 \times 10^7$-fold or more amplification, about $1 \times 10^8$-fold or more amplification, about $1 \times 10^9$-fold or more amplification, or about $1 \times 10^{10}$-fold or more amplification in the time frame of the reaction, for example, in 5, 10 or twelve minutes. The reaction is highly sensitive, and is able to detect, for example, as low as about 1, 2, 3, 4, 5, 6, 7, 8, 9, 10, 20, 30, 40, 50, 60, 70, 80, 90, or 100 copies, or more, in a sample, as many as 200, 500, 1,000, 5,000, or 10,000, or more copies in a sample, or, for example, may detect a target that is present at a concentration of, for example, about 3.32E-13 micromolar to about 3.32E-8 micromolar, about 1.66E-12 micromolar to about 3.32E-8 micromolar, about 3.32E-13 micromolar to about 3.32E-7 micromolar, or about 3.32E-13 micromolar to about 3.32E-6 micromolar.

NEAR methods are disclosed, e.g., in U.S. 2009/0081670 and U.S. 2009/0017453 each of which are incorporated herein by reference.

The isothermal nature of NEAR, coupled with the production of short products and geometric amplification of either DNA or RNA targets, provides an ultra-rapid amplification method. As disclosed herein, coupling of this approach to a real-time fluorescence detection approach provides exquisite sensitivity and specificity. Further, NEAR is distinguished from most molecular tests as there is no need for a lengthy or cumbersome sample preparation/nucleic acid purification. These key attributes make NEAR an ideal technology for point-of-care (POC) integration, where a rapid and reliable result is essential. Based on these principles, the present disclosure provides a NEAR assay to detect the presence of the bacterium *Streptococcus pyogenes* (GAS or StrepA) when present in a biological sample, e.g., a clinical throat swab sample.

Nucleic acids (e.g., polynucleotides) suitable for amplification in connection with the present methods include double-stranded and single-stranded nucleic acid molecules, such as DNA and RNA molecules. The polynucleotides may be of genomic, chromosomal, plasmid, mitochondrial, cellular, and viral nucleic acid origin. For double stranded polynucleotides, the amplification may be of either one or both strands.

Another such isothermal amplification method suitable for the methods disclose herein is Recombinase Polymerase Amplification (RPA). RPA can allow users to detect a particular sequence in trace amounts, facilitating point-of-care testing and increasing the accessibility and speed of diagnostics. As described here, RPA employs enzymes, known as recombinases, that are capable of pairing oligonucleotide primers with homologous sequences in template double-stranded nucleic acid. In this way, DNA synthesis is directed to defined points in a template double-stranded nucleic acid. Using two or more sequence-specific (e.g., gene-specific) primers, an exponential amplification reaction is initiated if the template nucleic acid is present. The reaction progresses rapidly and results in specific amplification of a sequence present within the template double-stranded nucleic acid from just a few copies of the template nucleic acid to detectable levels of the amplified products within minutes. RPA methods are disclosed, e.g., in U.S. Pat. Nos. 7,270,981; 7,399,590; 7,666,598; 7,435,561; US 2009/0029421; and WO 2010/141940, all of which are incorporated herein by reference.

The terms "templates" and "primers" are used interchangeably and refer generally to an oligonucleotide sequence that serves as a starting point for nucleotide amplification of a target sequence using a polymerase. Templates are defined as oligonucleotides that bind to a recognition region of a target sequence and also contain a nicking enzyme binding region upstream of the recognition region and a stabilizing region upstream to the nicking enzyme binding region. The compositions disclosed herein can contain a set of templates that amplify the target nucleic acid sequence. The templates can comprise sequences that are complementary to the target nucleic acid sequence or that differ from the target nucleic acid sequence at one or more positions. Design of templates suitable for NEAR amplification methods disclosed herein are provided in, for example, U.S. 2009/0081670 and U.S. 2009/0017453, each of which are incorporated herein by reference.

The templates of the present methods may include, for example, spacers, blocking groups, and modified nucleotides. Modified nucleotides are nucleotides or nucleotide triphosphates that differ in composition and/or structure from natural nucleotides and nucleotide triphosphates. Modifications include those naturally occurring that result from modification by enzymes that modify nucleotides, such as methyltransferases. Modified nucleotides also include synthetic or non-naturally occurring nucleotides. For example, modified nucleotides include those with 2' modifications, such as 2'-O-methyl and 2'-fluoro. Other 2'-modified nucleotides are known in the art and are described in, for example U.S. Pat. No. 9,096,897, which is incorporated herein by reference in its entirety. Modified nucleotides or nucleotide triphosphates used herein may, for example, be modified in such a way that, when the modifications are present on one strand of a double-stranded nucleic acid where there is a restriction endonuclease recognition site, the modified nucleotide or nucleotide triphosphates protect the modified strand against cleavage by restriction enzymes. Thus, the presence of the modified nucleotides or nucleotide triphosphates encourages the nicking rather than the cleavage of the double-stranded nucleic acid. Blocking groups are chemical moieties that can be added to the template to inhibit target sequence-independent nucleic acid polymerization by the polymerase. Blocking groups are usually located at the 3' end of the template. Examples of blocking groups include, for example, alkyl groups, non-nucleotide linkers, phosphorothioate, alkane-diol residues, peptide nucleic acid, and nucleotide derivatives lacking a 3'-OH, including, for example, cordycepin. Examples of spacers, include, for example, C3 spacers. Spacers may be used, for example, within the template, and also, for example, at the 5' end to attach other groups, such as, for example, labels.

In another aspect of the invention, there is provided a method for detection of *S. pyogenes* in a sample comprising the steps of obtaining a tissue sample from a subject; extracting nucleic acids from the sample; and amplifying the nucleic acid; wherein the nucleic acid is amplified and detected with templates and probes as described herein.

The present invention further comprises detecting the amplification product, for example, by a method selected from the group consisting of gel electrophoresis, mass spectrometry, SYBR I fluorescence, SYBR II fluorescence, SYBR Gold, Pico Green, TOTO-3, intercalating dye detection, FRET, molecular beacon detection, surface capture, capillary electrophoresis, incorporation of labeled nucleotides to allow detection by capture, fluorescence polarization, and lateral flow capture. Amplification products can be detected, for example, by chemical moieties that intercalate into double-stranded DNA. For example, SYBR Green® binds double-stranded DNA and upon excitation emit light; thus as product accumulates, fluorescence increases. The amplification products may be, for example, detected using a solid surface method, for example, where at least one capture probe is immobilized on the solid surface that binds to the amplified sequence. In some embodiments of all aspects, detecting the amplified product is performed using "real-time fluorescence."

The term "real-time fluorescence," refers to the detection of nucleic acid amplification products via a fluorescent signal generated by the coupling of a fluorogenic dye molecule and a quencher moiety to the same or different oligonucleotide substrates. Examples of commonly used probes are TAQMAN® probes, Molecular Beacon probes, and SCORPION® probes. Briefly, TAQMAN® probes, Molecular Beacons, and SCORPION® probes each have a fluorescent reporter dye (also called a "fluor") and a quencher moiety attached in close proximity to one another. In the unhybridized state, the proximity of the fluor and the quencher molecules prevents the detection of fluorescent signal from the probe; in the case of TAQMAN® probes, during amplification, when the polymerase replicates a template on which a probe is bound, the 5'-nuclease activity of the polymerase cleaves the probe thus, increasing fluorescence with each replication cycle as the fluor and quencher are separated from one another. Molecular beacons probes emit fluorescence following annealing of a homologous product, as this event induces a conformational change in the structure of the beacon, thereby separating the fluor and quencher. Briefly, TAQMAN® probes and SCORPION® probes, similar to Molecular beacons, will release fluorescence signal when a specific product anneals to the probe and is extended, which leads to separation of the fluor and quencher.

The production or presence of target nucleic acids and nucleic acid sequences may also be detected and monitored by lateral flow devices. Lateral Flow devices are well known. These devices generally include a solid phase fluid permeable flow path through which fluid flows through by capillary force. Examples include, but are not limited to, dipstick assays and thin layer chromatographic plates with various appropriate coatings. Immobilized on the flow path are various binding reagents for the sample, binding partners or conjugates involving binding partners for the sample and signal producing systems. Detection of samples can be achieved in several manners; enzymatic detection, nanoparticle detection, colorimetric detection, and fluorescence detection, for example. Enzymatic detection may involve enzyme-labeled probes that are hybridized to complementary or substantially complementary nucleic acid targets on the surface of the lateral flow device. The resulting complex can be treated with appropriate markers to develop a readable signal. Nanoparticle detection involves bead technology that may use colloidal gold, latex and paramagnetic nanoparticles. In one example, beads may be conjugated to an anti-biotin antibody. Target sequences may be directly biotinylated, or target sequences may be hybridized to a sequence specific biotinylated probes. Gold and latex give rise to colorimetric signals visible to the naked eye and paramagnetic particles give rise to a non-visual signal when excited in a magnetic field and can be interpreted by a specialized reader.

Nucleic acids can also be captured on lateral flow devices. Means of capture may include antibody dependent and antibody independent methods. Antibody-dependent capture generally comprises an antibody capture line and a labeled probe that is complementary or substantially complementary sequence to the target. Antibody-independent capture generally uses non-covalent interactions between two binding partners, for example, the high affinity and irreversible linkage between a biotinylated probe and a Strep Avidin line. Capture probes may be immobilized directly on lateral flow membranes. Both antibody dependent and antibody independent methods may be used in multiplexing.

The production or presence of target nucleic acids and nucleic acid sequences may also be detected and monitored by multiplex DNA sequencing. Multiplex DNA sequencing is a means of identifying target DNA sequences from a pool of DNA. The technique allows for the simultaneous processing of many sequencing templates. Pooled multiple templates can be resolved into individual sequences at the completion of process.

The terms "complementary" and "substantially complementary" refer to base pairing between nucleotides or nucleic acids, such as, for instance, between the two strands of a double-stranded DNA molecule or between an oligonucleotide primer and a primer binding site on a single-stranded nucleic acid to be sequenced or amplified. Complementary nucleotides are, generally, A and T (or A and U), and G and C. Within the context of the present invention, it is to be understood that the specific sequence lengths listed are illustrative and not limiting and that sequences covering the same map positions, but having slightly fewer or greater numbers of bases are deemed to be equivalents of the sequences and fall within the scope of the invention, provided they will hybridize to the same positions on the target as the listed sequences. Because it is understood that nucleic acids do not require complete complementarity in order to hybridize, the probe and primer sequences disclosed herein may be modified to some extent without loss of utility as specific primers and probes. Generally, sequences having homology of 80%, 90%, 95%, 97%, 98%, 99% fall within the scope of the present invention. As is known in the art, hybridization of complementary and partially complementary nucleic acid sequences may be obtained by adjustment of the hybridization conditions to increase or decrease stringency, i.e., by adjustment of hybridization temperature or salt content of the buffer.

In some embodiments of all aspects, the template and probes can be labeled with (e.g., conjugated to) a detectable label. The term "detectable label" and "label" as used herein refers to any chemical moiety that can be used to provide a detectable (preferably quantifiable) signal, and that can be attached to a nucleic acid or protein via a covalent bond or noncovalent interaction (e.g., through ionic or hydrogen bonding, or via immobilization, adsorption, or the like). Labels generally provide signals detectable by fluorescence, chemiluminescence, radioactivity, colorimetry, mass spectrometry, X-ray diffraction or absorption, magnetism, enzymatic activity, or the like. Examples of labels include haptens, enzymes, enzyme substrates, coenzymes, enzyme inhibitors, fluorophores, quenchers, chromophores, magnetic particles or beads, redox sensitive moieties (e.g., electrochemically active moieties), luminescent markers, radioisotopes (including radionucleotides), and members of binding pairs. More specific examples include fluorescein, phycobiliprotein, tetraethyl rhodamine, and beta-galactosidase. Binding pairs may include biotin/Strepavidin, biotin/avidin, biotin/neutravidin, biotin/captavidin, epitope/antibody, protein A/immunoglobulin, protein G/immunoglobulin, protein L/immunoglobulin, GST/glutathione, His-tag/Metal ion (e.g., nickel, cobalt or copper), antigen/antibody, FLAG/M1 antibody, maltose binding protein/maltose, calmodulin binding protein/calmodulin, enzyme-enzyme substrate, receptor-ligand binding pairs, and analogs and mutants of the binding pairs.

As used herein, the terms "fluorescence label" and "fluorophore" are used interchangeably and refer to any substance that emits electromagnetic energy at a certain wavelength (emission wavelength) when the substance is illuminated by radiation of a different wavelength (excitation wavelength) and is intended to encompass a chemical or biochemical molecule or fragments thereof that is capable of interacting or reacting specifically with an analyte of interest in a sample to provide one or more optical signals.

Representative fluorophores for use in the methods provided herein include, for example, FAM, (tetramethylrhodamine) Texas Red™, green fluorescent protein, blue fluorescent protein, red fluorescent protein, fluorescein, fluorescein 5-isothiocyanate (FITC), cyanine dyes (Cy3, Cy3.5, Cy5, Cy5.5, Cy7), Bodipy dyes (Invitrogen) and/or Alexa Fluor dyes (Invitrogen), dansyl, Dansyl Chloride (DNS-C1), 5-(iodoacetamida)fluorescein (5-IAF, 6-acryloyl-2-dimethylaminonaphthalene (acrylodan), 7-nitrobenzo-2-oxa-1,3-diazol-4-yl chloride (NBD-C1), ethidium bromide, *Lucifer* Yellow, rhodamine dyes (5-carboxyrhodamine 6G hydrochloride, Lissamine rhodamine B sulfonyl chloride, rhodamine-B-isothiocyanate (RITC (rhodamine-B-isothiocyanate), rhodamine 800); tetramethylrhodamine 5-(and 6-)isothiocyanate (TRITC)), Texas Red™, sulfonyl chloride, naphthalamine sulfonic acids including but not limited to 1-anilinonaphthalene-8-sulfonic acid (ANS) and 6-(p-toluidinyl)naphthalen-e-2-sulfonic acid (TNS), Anthroyl fatty acid, DPH, Parinaric acid, TMA-DPH, Fluorenyl fatty acid, Fluorescein-phosphatidylethanolamine, Texas red-phosphatidylethanolamine, Pyrenyl-phophatidylcholine, Fluorenyl-phosphotidylcholine, Merocyanine 540, Naphtyl Styryl, 3,3'dipropylthiadicarbocyanine (diS-C3-(5)), 4-(p-dipentyl aminostyryl)-1-methylpyridinium (di-5-ASP), Cy-3 lodo Acetamide, Cy-5-N-Hydroxysuccinimide, Cy-7-Isothiocyanate, IR-125, Thiazole Orange, Azure B, Nile Blue, Al Phthalocyanine, Oxaxine 1, 4', 6-diamidino-2-phenylindole. (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofiuors, Coronene, and metal-ligand complexes.

It should be noted that a fluorescence quencher is also considered a detectable label. For example, the fluorescence quencher may be contacted to a fluorescent dye and the amount of quenching may be detected.

Haptens for use in the methods provided herein include, for example, digoxigenin, glutathione and biotin.

Enzymes for use in the methods provided herein include, for example, alkaline phosphatase (AP), beta-galactosidase, horse radish peroxidase (HRP), soy bean peroxidase (SBP), urease, beta-lactamase and glucose oxidase.

The compositions for detecting the presence or absence of *S. pyogenes* in a biological sample described herein, e.g., reagent mixtures, can include a DNA polymerase. The DNA polymerase disclosed herein may be a eukaryotic or prokaryotic polymerase. The polymerase may be selected from, for example, *Geobacillus bogazici* DNA polymerase, Bst DNA polymerase, Bst DNA polymerase (Large fragment), 9° Nm DNA polymerase, Phi29 DNA polymerase, DNA polymerase I (*E. coli*), DNA polymerase I, Large, (Klenow) fragment, Klenow fragment (3'-5' exo-), T4 DNA polymerase, T7 DNA polymerase, Deep VentR™ (exo-) DNA Polymerase, Deep VentR™ DNA Polymerase, DyNAzyme™ EXT DNA, DyNAzyme™ II Hot Start DNA Polymerase, Phusion™ High-Fidelity DNA Polymerase, Therminator™ DNA Polymerase, Therminator™ II DNA Polymerase, VentR® DNA Polymerase, VentR® (exo-) DNA Polymerase, RepliPHI™ Phi29 DNA Polymerase, rBst DNA Polymerase, rBst DNA Polymerase, Large Fragment (IsoTherm™ DNA Polymerase), MasterAmp™ AmpliTherm™ DNA Polymerase, Taq DNA polymerase, Tth DNA polymerase, Tfl DNA polymerase, Tgo DNA polymerase, SP6 DNA polymerase, Tbr DNA polymerase, DNA polymerase Beta, ThermoPhi DNA polymerase and Pyrophage 3173 (Lucigen), or combinations thereof.

The compositions for detecting the presence or absence of *S. pyogenes* in a biological sample described herein, such as reagent mixtures and buffered solutions, can include an antimicrobial agent or preservative. An antimicrobial agent can inhibit the growth of microorganisms and increase the shelf life of a reagent mixture or buffer solution. The antimicrobial agent can include benzalkonium chloride, 5-chloro-2-methyl-4-isothiazolin-3-one, 2-methyl-4-isothiazolin-3-one, ProClin® (e.g., ProClin 300®, ProClin® 950, etc.), azides, merthiolates, and/or antibiotics. In some embodiments, the antimicrobial agent includes 5-chloro-2-methyl-4-isothiazolin-3-one and 2-methyl-4-isothiazolin-3-one.

By "constant temperature," "isothermal conditions," "essentially isothermal," or "isothermally" is meant a set of reaction conditions where the temperature of the reaction is kept essentially or substantially constant during the course of the amplification reaction. An advantage of the amplification method of the present methods is that the temperature does not need to be cycled between an upper temperature and a lower temperature. The nicking and the extension reaction will work at the same temperature or within the same narrow temperature range. However, it is not necessary that the temperature be maintained at precisely one temperature. If the equipment used to maintain an elevated temperature allows the temperature of the reaction mixture to vary by a few degrees, or few tenths of a degree, such as, for example, less than 1 degree, 0.8 degrees, 0.6 degrees, 0.4 degrees, or 0.2 degrees, this is not detrimental to the amplification reaction, and may still be considered to be an isothermal reaction.

The present invention may be used for multiplex amplification. Thus, for example, in certain embodiments of the present invention at least two target sequences are capable of being amplified. The term "multiplex amplification" refers to the amplification of more than one nucleic acid of interest. By "capable of being amplified" is meant the amplification reaction comprises the appropriate templates and enzymes to amplify at least two target sequences. Thus, for example, the amplification reaction may be prepared to detect at least two target sequences, but only one of the target sequences may actually be present in the sample being tested, such that both sequences are capable of being amplified, even though only one sequence may actually be amplified. Or, where two target sequences are present, the amplification reaction may result in the amplification of both of the target sequences. The multiplex amplification reaction may result in the amplification of one, some, or all, of the target sequences for which it comprises the appropriate templates and enzymes.

As used herein, the term "biological sample" or "sample" refers to a sample obtained or derived from a subject (i.e., a patient). By way of example, the biological sample may be a tissue fluid obtained from a subject, which may be selected from the group consisting of blood, plasma, serum, lymphatic fluid, synovial fluid, cerebrospinal fluid, amniotic fluid, amniotic cord blood, tears, saliva, mucus secretions, urine and nasopharyngeal washes. Representative biological samples from the respiratory tract include wound and throat swabs, throat washings, nasal swabs, and specimens from the lower respiratory tract.

As used herein, "obtain" or "obtaining" can be any means whereby one comes into possession of the sample by "direct" or "indirect" means. Directly obtaining a sample means performing a process (e.g., performing a physical method such as extraction) to obtain the sample. Indirectly obtaining a sample refers to receiving the sample from another party or source (e.g., a third party laboratory that directly acquired the sample). Directly obtaining a sample includes performing a process that includes a physical change in a physical substance, e.g., a starting material, such as a blood, e.g., blood that was previously isolated from a patient. Thus, obtain is used to mean collection and/or removal of the sample from the subject. Furthermore, "obtain" is also used to mean where one receives the sample from another who was in possession of the sample previously.

The term "subject" refers to an animal or human, or to one or more cells derived from an animal or human. Preferably, the subject is a human. Subjects can also include non-human primates. Cells may be in any form, including but not limited to cells retained in tissue, cell clusters, immortalized, transfected or transformed cells, and cells derived from an animal that has been physically or phenotypically altered. A human subject can be known as a patient.

In yet other embodiments, a kit is provided for following the methods of the present invention for nucleic acid amplification, comprising a DNA polymerase; a first template for nucleic acid amplification, comprising a recognition region at the 3' end that is complementary or substantially complementary to the 3' end of a target sequence antisense strand; a nicking enzyme binding site and a nicking site upstream of said recognition region; and a stabilizing region upstream of said nicking enzyme binding site and said nicking site; a second template for nucleic acid amplification, comprising a recognition region at the 3' end that is complementary or substantially complementary to the 3' end of a target sequence sense strand; nicking enzyme binding site and a nicking site upstream of said recognition region; and a stabilizing region upstream of said nicking enzyme binding site and said nicking site; one or more nicking enzymes, wherein either one enzyme is capable of nicking at the nicking site of said first and said second templates, or a first enzyme is capable of nicking at the nicking site of said first primer and a second enzyme is capable of nicking at the enzyme site of said second primer.

The kits used for the present methods may also comprise one or more of the components in any number of separate containers, packets, tubes, vials, microtiter plates and the like, or the components may be combined in various combinations in such containers.

The components of the kit may, for example, be present in one or more containers, for example, all of the components may be in one container, or, for example, the enzymes may be in a separate container from the templates. The components may, for example, be lyophilized, freeze dried, or in a stable buffer. In one example, the polymerase and nicking enzymes are in lyophilized form in a single container, and the templates are either lyophilized, freeze dried, or in buffer, in a different container. Or, in another example, the polymerase, nicking enzymes, and the templates are, in lyophilized form, in a single container. Or, the polymerase and the nicking enzyme may be separated into different containers.

Kits may further comprise, for example, dNTPs used in the reaction, or modified nucleotides, cuvettes or other containers used for the reaction, or a vial of water or buffer for re-hydrating lyophilized components. The buffer used may, for example, be appropriate for both polymerase and nicking enzyme activity.

The kits used for the present methods may also comprise instructions for performing one or more methods described herein and/or a description of one or more compositions or reagents described herein. Instructions and/or descriptions may be in printed form and may be included in a kit insert. A kit also may include a written description of an Internet location that provides such instructions or descriptions.

Kits may further comprise reagents used for detection methods, such as, for example, reagents used for FRET, lateral flow devices, dipsticks, fluorescent dye, colloidal gold particles, latex particles, a molecular beacon, or polystyrene beads.

An advantage of the present methods and the present kits is that they can be used in any device that provides a constant temperature, including thermocyclers, incubation ovens, water baths, and heat blocks.

Methods using capture probes for detection include, for example, the use of a nucleic acid molecule (the capture probe) comprising a sequence that is complementary to, or substantially complementary to, an amplification product strand such that the capture probe binds to amplified nucleic acid. The probe may be linked to a detectable label in certain embodiments, and amplification product may be detected based on the detectable label of the probe specifically hybridized to the amplification product. The reaction may, for example, further comprise an antibody directed against a molecule incorporated into or attached to the capture probe. Or, for example, the capture probe, or a molecule that binds to the capture probe, may incorporate, for example, an enzyme label, for example, peroxidase, alkaline phosphatase, or beta-galactosidase, a fluorescent label, such as, for example, fluorescein or rhodamine, or, for example, other molecules having chemiluminescent or bioluminescent activity. In some embodiments, the probe is linked to a solid support, and amplification product strands may be specifically immobilized to the capture probe linked to the solid support under conditions known and selected by the person of ordinary skill in the art. In the latter embodiments, a solid support-immobilized amplification product may be subjected to processing steps, such as washing, ion exchange, release from the solid support, or other processing steps. An amplification product may be detected when immobilized to a solid support in some embodiments. The embodiments of the present invention also comprise combinations of these detection and analysis methods.

In yet another embodiment, the methods further comprise modifying the subject's clinical record to identify the subject as being diagnosed as having a *S. pyogenes* infection. Preferably, the clinical record is stored in a computer readable medium.

EXAMPLES

The invention is further described in the following examples, which do not limit the scope of the invention eters that are common to most nucleic acid amplification technologies. Using these filtering criteria, a final set of GAS template sets were selected for screening.

The screening process resulted in the development of at least one GAS assay.

The assay targets the cell envelope proteinase A (cepA) gene. This gene encodes for the interleukin-8 cleaving enzyme, which is used by *S. pyogenes* to inactivate the neutrophil chemoattractant interleukin-8. The cepA 3062 assay targets position 345,952-345,994 of the GAS reference strain M1 (NC_002737.1) and position 1,833-1,874 of the cepA gene. The assay templates, probe (molecular beacon) and product sequences are provided in Table 1. The probe is labeled with FAM reporter and BHQ-1 quencher.

TABLE 1

| ID | Sequence (5'/3') | Oligo [ ] |
|---|---|---|
| Template 1a-Spy cepA s3062 F30 | AGACTCCATATGGAGTCTAGCCAAACAG GAACA (SEQ ID NO: 1) | 500 nM |
| Template 2a-Spy cepA s3062 R41m | CGACTCCATATGGAGTCGaaAGCAATCT GAGGA (SEQ ID NO: 2) | 100 nM |
| Template 1b-Spy cepA F30b.5om | AGACTCCACACGGAGTCTAGCCAAACAG mGmAmAmCmA (SEQ ID NO: 8) | 500 nM |
| Template 2b-Spy cepA R41m.1b.5om | GGACTCCACACGGAGTCCGCCAGCAATC mUmGmAmGmG (SEQ ID NO: 9) | 100 nM |
| Molecular beacon-Spy.cepA.S4.P1.MB4 (Fam/BHQ1) | ACAAGTATGTGAGGAGAGGCCATACTTG T (SEQ ID NO: 3) | 200 nM |
| Product 1 | CAAACAGGAACAAGTATGGCCTCTCCTC AGATTGC (SEQ ID NO: 4) | |
| Product 2 | GCAATCTGAGGAGAGGCCATACTTGTTC CTGTTTG (SEQ ID NO: 5) | | described in the claims. Those of ordinary skill in the art understand that for an exemplary assay, numerous modifications may be made to the volumes and format of the reaction, the length of time that the assay is conducted, and the amounts of each reactant.

NEAR of *Streptococcus pyogenes* Genomic DNA
Target Selection

A NEAR assay targeting GAS was developed that is unique to GAS while showing conservation across all strains and isolates of GAS found in the public domain at the time this analysis was performed. Initial bioinformatics analyses were performed using sequence data available at the time from NCBI's Nucleotide Database (www.ncbi.nlm.nih.gov/nuccure) and Genome Database (www.ncbi.nlm.nih.gov/genome?db=genome). Multiple sequence alignments to identify regions of conservation were performed and multiple regions within the GAS genome were strongly conserved. All sequence segments that did show homology were subjected to BLAST analysis to determine whether these sequences were unique to GAS. Following BLAST analyses, all sequences identified as unique to GAS were used for template set generation (BLAST analysis performed using the nucleotide collection (nr/nt) database). Template sets were generated using an in-house automated software tool. In silico filtering was then applied to finalize the selection of template sets to screen in the laboratory. In general, these filtering criteria involved analyzing the template sets for potential interactions that could reduce assay performance, including several parameters identified in-house that might specifically impact NEAR performance as well as param- To confirm that the targeted sequence was conserved among all GAS cepA sequences found in the public domain as well as unique to GAS, multiple sequence alignments and BLAST analyses were performed. Multiple alignment analysis of these sequences showed complete homology for the region of the gene targeted by the 3062 assay. Further, there are currently 24 complete GAS genomes (including whole genome shotgun sequence) available for sequence analysis in NCBI Genome. The cepA gene is present in all 24 genomes, and the 3062 target region within cepA is conserved among all 24 genomes. Upon BLAST analysis, it was confirmed that no other species contain significant homology to the 3062 target sequence.

Assay Development

As a reference, the reagent mixtures discussed below are annotated as follows: 25C-4× lyophilization mix, single tube assay format; 50C-2×lyophilization mix, single tube assay format; 25T-4× lyophilization mix, target assay only; 50T-2×lyophilization mix, target assay only; 25I-4× lyophilization mix, IC assay only; 50I-2×lyophilization mix, internal control (IC) assay only.

The GAS NEAR assay can be run on an appropriate platform. For example, the GAS NEAR assay can be run on an Alere i platform (www.alere.com/ww/en/product-details/alere-i-strep-a.html). An Alere i system consists of an instrument which provides heating, mixing and fluorescence detection with automated result output, and a set of disposables, consisting of the sample receiver (where the elution buffer is stored), a test base (containing two tubes of lyophilized NEAR reagents) and a transfer device (designed to transfer 100 µl aliquots of eluted sample from the sample receiver to each of the two tubes containing lyophilized NEAR reagents located in the test base). Suitable disposables for use with the Alere i GAS NEAR test include those described in, for example U.S. application Ser. No. 13/242,999, incorporated herein by reference in its entirety.

In addition to containing the reagents necessary for driving the GAS NEAR assay, the lyophilized material also contains the lytic agent for GAS, the protein plyC; therefore, GAS lysis does not occur until the lyophilized material is re-suspended. In some cases, the lyophilized material does not contain a lytic agent for GAS, for example, in some examples, the lyophilized material does not contain the protein plyC. The elution buffer was designed to allow for the rapid release of GAS organisms from clinical sample throat swabs as well as to provide the necessary salts for driving the NEAR assay (both MgSO4 and (NH4)2SO4), in a slightly basic environment. In some examples, the elution buffer also includes an anti-microbial agent or preservative (e.g., ProClin® 950).

For the present examples, GAS assay was performed as a two tube assay—a GAS target specific assay in one tube, and an internal control (IC) assay in a second tube (tested side by side on the Alere i).

Assay Performance:

FIG. 1 shows the results of a limits of detection (LOD) study performed using the GAS assay under various conditions. The LOD study was performed using a standard NEAR 'hot start' approach where the sample and lyophilized mix were both pre-heated at 56←C for 3 minutes and then combined. Comparing the four mixes to one another, it is clear that the target only assays (25T & 50T) perform more robustly than the combined or complete (25C & 50C) assays, especially at low copy number. From these data it was concluded that the LOD is 10-25 copies of purified genomic DNA for mixes 25T & 50T, 25 copies for mix 25C and 50 copies for mix 50C, when a standard 'hot start' approach is used.

Internal Control (IC):

An IC assay was developed using a DNA oligonucleotide designed to serve as the IC target, and a molecular beacon was designed to specifically detect the product generated off of the IC target (representative oligonucleotides can be found in Table 2). This DNA oligonucleotide contains 5' and 3' ends that are complementary to the target template set's recognition regions but with a spacer region that differs from the target's spacer region. Thus, the same template set is used to amplify both target and IC.

0 to 250 copies of purified GAS gDNA). In all instances, the 25C mix either outperformed or was equivalent to the 50C mix.

Figure 3:
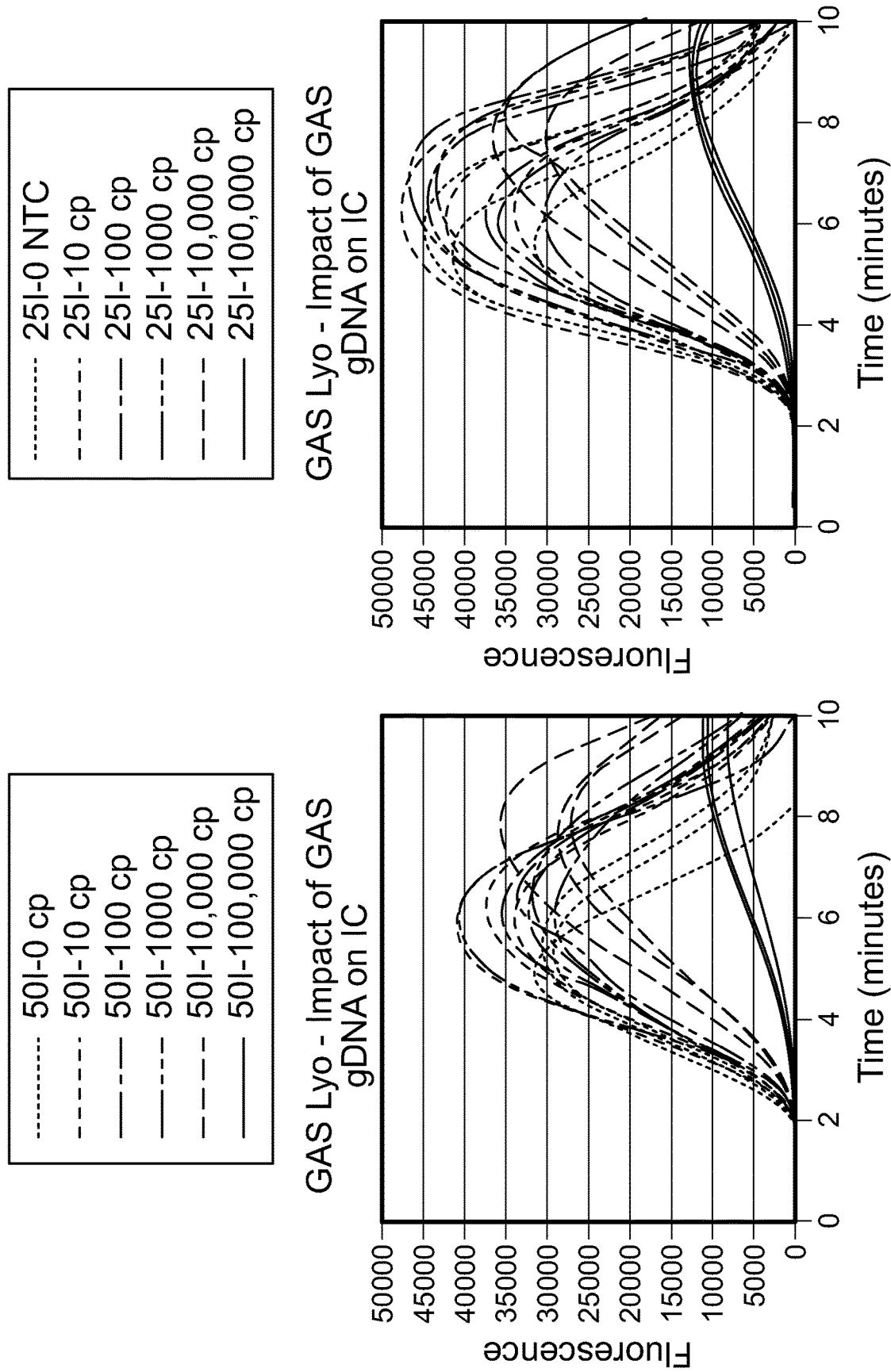
FIG. 3 shows the results of an exemplary GAS IC assay (25I & 50I) performed in the presence of increasing amounts of GAS genomic DNA to assess the impact of this inhibitor on target assay performance.

Shown in FIG. 3 are the results of a similar experiment where the 25I and 50I mixes were compared in the presence of 0-100,000 copies of purified GAS gDNA. The GAS IC assay showed robust performance in the presence of a large amount of GAS gDNA, with no significant impact on performance until 100,000 copies of GAS gDNA was present in the reaction. When no GAS target was present, both mixes showed strong IC amplification and detection. Further, up to 1000 copies of GAS target had minimal if any impact on IC performance. Even at 10,000 copies of GAS target the IC signal was still robust for both mix types. It was not until 100,000 copies of GAS target was added that a significant reduction in performance was found, and even at this copy number amplification was still clearly well above background levels for both the 25I and 50I mixes. Overall, the 25I showed slightly stronger fluorescence than the 50I mix.

Lyophilization:

In order to provide a viable point of care (POC) technology, the reagents used for GAS detection need to be stable for an extended period of time at ambient temperature, or at minimum when stored at 2-8° C. For example, a minimum of six months storage at 2-8° C. without a loss in performance is recommended, with the goal being 2-3 years. In order to provide this level of stability, the NEAR assay reagents were lyophilized and subsequently packaged to minimize reagent exposure to both moisture and oxygen. To accomplish this, the NEAR assay reagents and lytic agent, plyC, were combined in a mix containing the excipients dextrose and trehalose and subjected to freeze drying. Optimization of both the mix composition and freeze drying method were performed to yield a suitable lyophilized mix that retained activity while providing long term stability. The final lyophilization mix and method selected are shown below in Table 3. The GAS assay format provides for two tubes, one tube providing the target assay and a second tube providing the IC assay. These reagents are freeze dried using the same lyophilization method and differ in composition only by the presence of the target molecular beacon in the target assay (& not in the IC assay) and the IC target oligo and IC molecular beacon in the IC assay (& not in the target

TABLE 2

Internal Control (IC) oligonucleotide and molecular beacon sequences.

| ID | Sequence (5'/3') | Oligo [ ] |
|---|---|---|
| Internal control molecular beacon-Flu B ICMB4 Rox (Rox/BHQ2) | TGTAGCTGACACCACCAAGCTACA (SEQ ID NO: 6) | 100 nM |
| Internal control oligo-Spy CepA.S4'.IC.3_11.11 | ACAATCTGAGGAGCTGACACCACCAAGC TACTGTTCCTGTTTA (SEQ ID NO: 7) | 10,000 copies |
| Internal control oligo-Spy CepA.S4'.IC_11.12 | GCAATCTGAGGAGCTGACACCACCAAGC TACTGTTCCTGTTTGA (SEQ ID NO: 10) | 200,000 copies |

Figure 2:
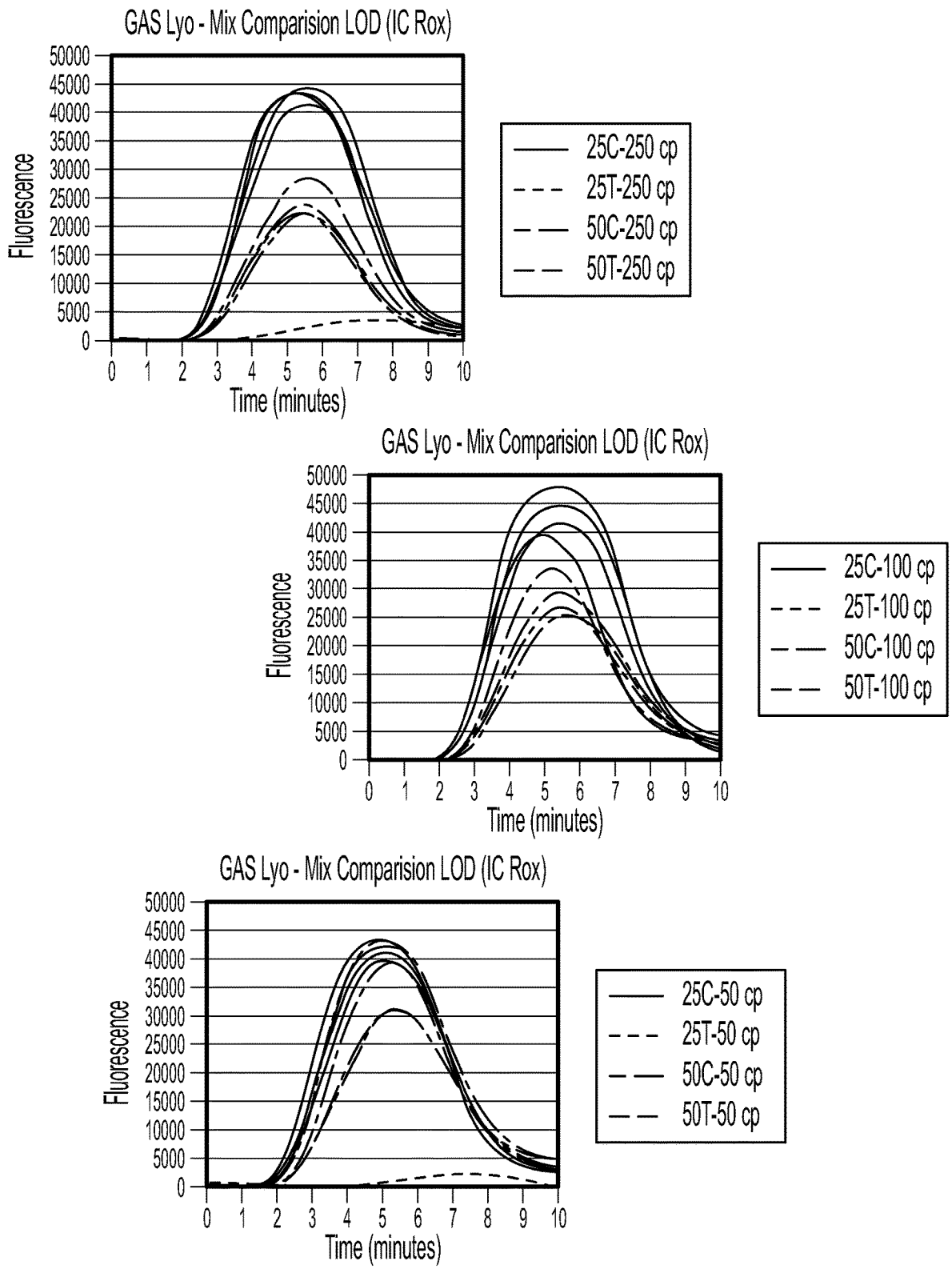
FIG. 2 shows the results of an exemplary LOD study performed comparing four mixes (25C—complete assay, 4×25 µl lyo pellet; 25T—target only assay, 4×25 µl lyo pellet; 50C—complete assay, 2×50 µl lyo pellet; 50T—target only assay, 2×50 µl lyo pellet). All reactions were performed on the Stratagene Mx3005P thermal cycler using a 'hot start' approach.
Figure 2:
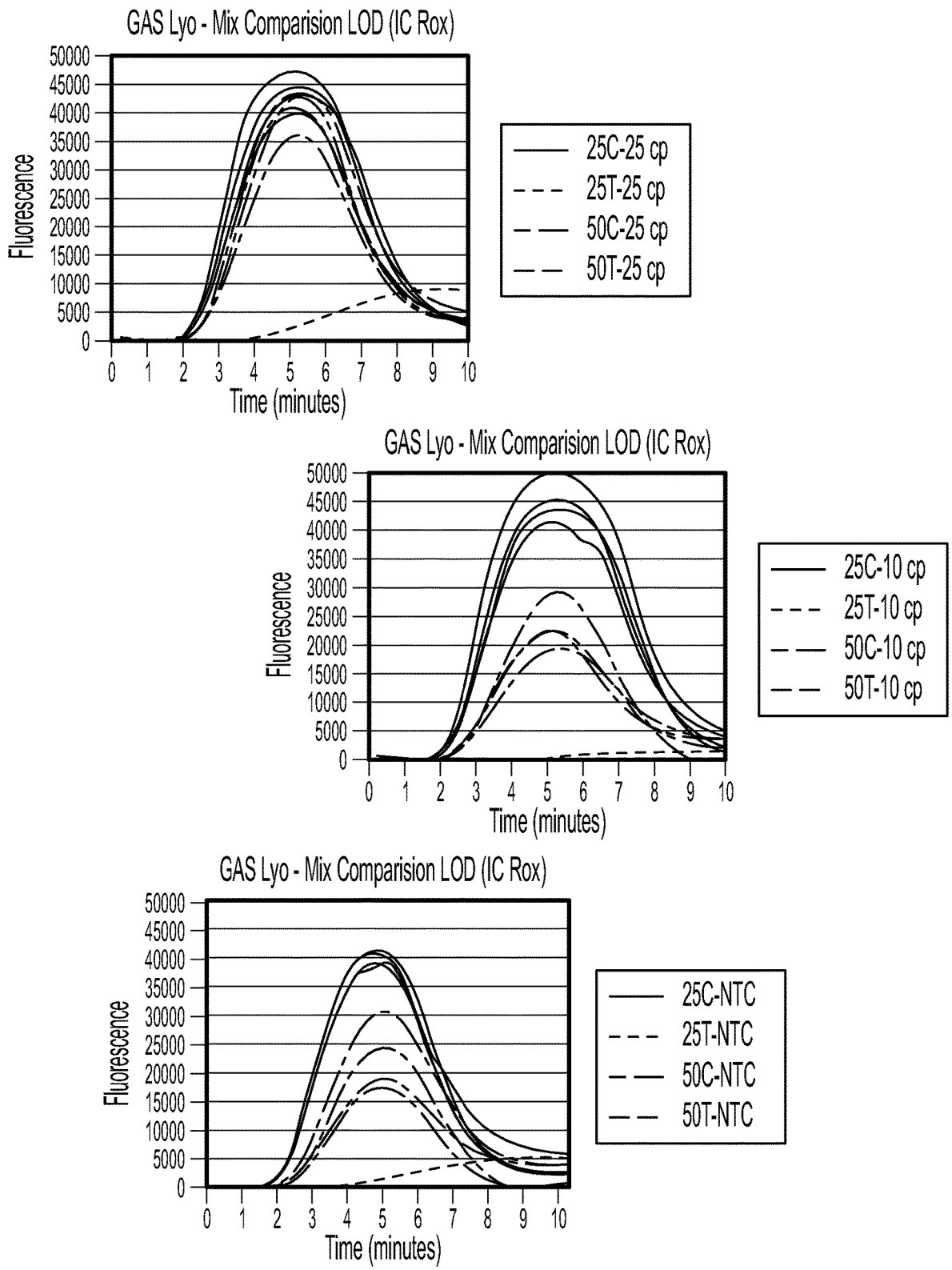

FIG. 2 shows the performance of the IC assay when combined with the target assay (25C and 50C mixes), under standard NEAR 'hot start' conditions. The results indicate robust IC performance in the presence of GAS gDNA (from assay). Both mixes are lyophilized as 2× (50 µl), meaning that the mixes are dried down at a 2× concentration and subsequently re-suspended in a 100 µl volume to provide a final 1× concentration of each reagent.

TABLE 3

GAS Lyophilization Mix - Reagent Composition

| Component | v1.0 | v2.0 |
| --- | --- | --- |
| Strep A (Target) Lyo Conditions | | |
| T1 | 500 nM F30 | 500 nM F30b.5om |
| T2 | 100 nM R41m | 100 nM R41m.1b.5om |
| Target MB | 200 nM MB4_FAM | 200 nM MB4_Fam |
| Pol (MG79) | 3.0. ug | 5.0 ug |
| NE | 30 U | 0.7 ug |
| ply C | 1 ug | 1 ug |
| Tris pH 8.0 | 50 mM | 50 mM |
| Dextran | Dextran 150 5% in 2x lyo | Dextran 500 5% in 2x lyo |
| Trehalose | 100 mM in 2x lyo | 100 mM in 2x lyo |
| dNTPS | 0.3 mM | 0.3 mM |
| $Na_2SO_4$ | 15 mM | 22.5 mM |
| Triton X-100 | 0.10% | 0.10% |
| DTT | 2 mM | 2 mM |
| Strep A (IC) Lyo Conditions | | |
| T1 | 500 nM F30 | 500 nM F30b.5om |
| T2 | 100 nM R41m | 100 nM R41m.1b.5om |
| IC | 10,000 copies IC3_11.1 | 200,000 copies IC_11.12 |
| IC MB | 100 nM IC_MB4_ROX | 100 nM IC_MB4_ROX |
| Pol (MG79) | 3.0 ug | 5.0 ug |
| NE | 30 U | 0.6 ug |
| ply C | 1 ug | — |
| Tris pH 8.0 | 50 mM | 50 mM |
| Dextran | Dextran 150 5% in 2x lyo | Dextran 500 5% in 2x lyo |
| Trehalose | 100 mM in 2x lyo | 100 mM in 2x lyo |
| dNTPs | 0.3 mM | 0.3 mM |
| $Na_2SO_4$ | 15 mM | 22.5 mM |
| Triton X-100 | 0.10% | 0.10% |
| DTT | 2 mM | 2 mM |

Shown in Table 3 are the final 1× reagent concentrations for the target and IC assays. The lyophilized materials are freeze dried at a 2× concentration (50 μl volume) and subsequently re-suspended in a 100 μl volume of elution buffer. In some cases, the two mixes are essentially identically except that the target only mix does not contain IC components and the IC only mix does not contain the target molecular beacon. In some cases, the mixes differ in that one mix includes plyC and another mix does not, for example, in some cases the IC mix does not contain plyC and the target mix contains plyC. In some cases, the mixes differ in the amount of NE, for example, in some cases the target mix contains 0.7 μg of NE and the IC mix contains 0.6 μg of NE.

GAS Lysis

Figure 4:
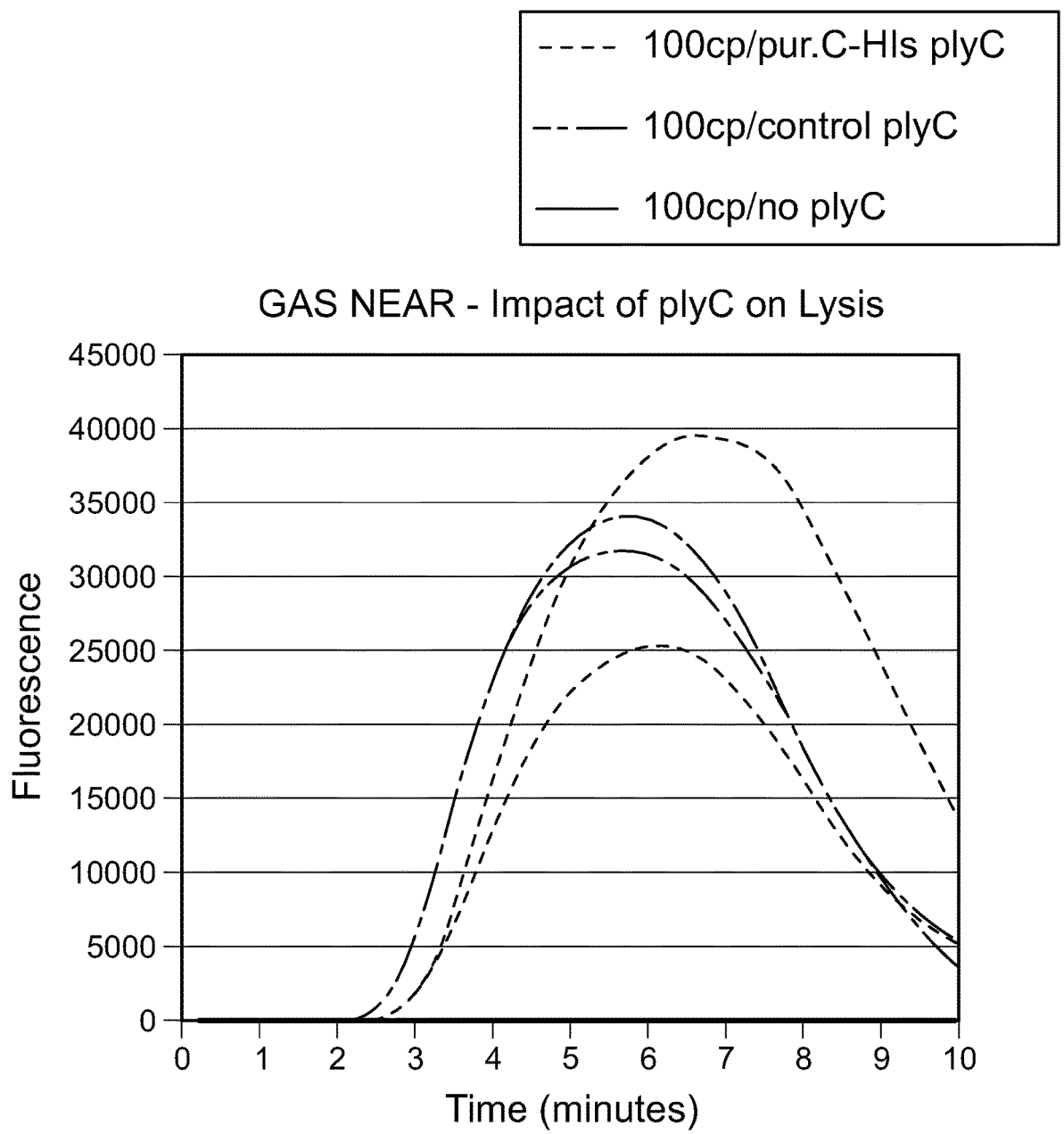
FIG. 4 depicts a typical wet GAS NEAR assay performed in the presence of 100 copies of inactivated GAS bacteria with or without 1 µg of plyC. Legend: pur. C-His plyC—C-terminus His-tagged plyC; control plyC—non-tagged plyC.

For optimal performance, the GAS organism is lysed to gain access to the target nucleic acid and allow for specific amplification and detection. The streptococcal bacteriophage C1 lysin plyC is able to rapidly lyse group A and C streptococci. Initial testing showed that the plyC protein provides rapid GAS bacterial lysis and further, that the presence of the protein does not interfere with NEAR assay performance (data not shown). Subsequently, it was shown that the protein can be lyophilized in combination with NEAR assay reagents and re-suspended to provide rapid, in silico GAS lysis allowing for sensitive and specific NEAR GAS target amplification and detection. To confirm that plyC can lyse GAS organisms under NEAR reaction conditions, and that it is necessary for NEAR detection of GAS, a 'hot start' experiment was performed where the detection of inactivated GAS organisms was tested plus or minus plyC (FIG. 4). In this experiment, 100 copies of inactivated GAS organisms were pre-heated to 56° C. and then combined with a mix of NEAR reagents containing 1 μg of plyC, and amplification was monitored for ten minutes using a fluorescently labeled molecular beacon. As shown in FIG. 4, if plyC was not present GAS was not detected (no fluorescent signal above background), but the presence of plyC enabled the rapid and robust detection of GAS, suggesting that the protein was able to readily lyse the target bacteria allowing access to the organism's genomic DNA.

Elution Buffer:

The GAS NEAR assay has been designed and developed to detect GAS collected from clinical throat swab samples. Each throat swab is eluted into 2.5 ml of an optimized buffer (Table 4) following a two-minute elution buffer pre-heat step (to reach a temperature of approximately 40° C. on the Alere i). The swab is dipped into the buffer briefly, swirled, and then removed. The buffer enables rapid elution off of the swab while also providing: 1) Tris pH 8.0 to provide buffering capacity, 2) the necessary salts to drive NEAR once it is used to re-suspend the NEAR lyophilized mix, 3) EDTA or EGTA to chelate any potential metal ions that inhibit NEAR and 4) the detergent Triton X-100 which is believed to help in the elution process as well as to disperse cell/cell debris clumping. The buffer can also include an anti-microbial agent, for example ProClin® 950. As will be described in later sections of this document, the elution buffer has been shown to effectively elute GAS from throat swabs and also to enable NEAR amplification and detection. Throat swab samples containing GAS have been eluted using this buffer and the eluate has been subsequently used to re-suspend NEAR lyophilized material, resulting in the amplification and detection of GAS originally present on the throat swabs.

TABLE 4

Elution Buffer Composition

| Reagent | v1.0 | v2.0 |
| --- | --- | --- |
| Tris-Cl, pH 8.0 | 10 mM | 10 mM |
| Triton X-100 | 0.10% | 0.10% |
| $(NH_4)_2SO_4$ | 15 mM | 15 mM |
| $MgSO_4$ | 15 mM | 15 mM |
| Chelating agent | 1 mM EDTA | 1 mM EGTA |
| Anti-microbial agent | — | 0.10% ProClin 950 |

Figure 5:
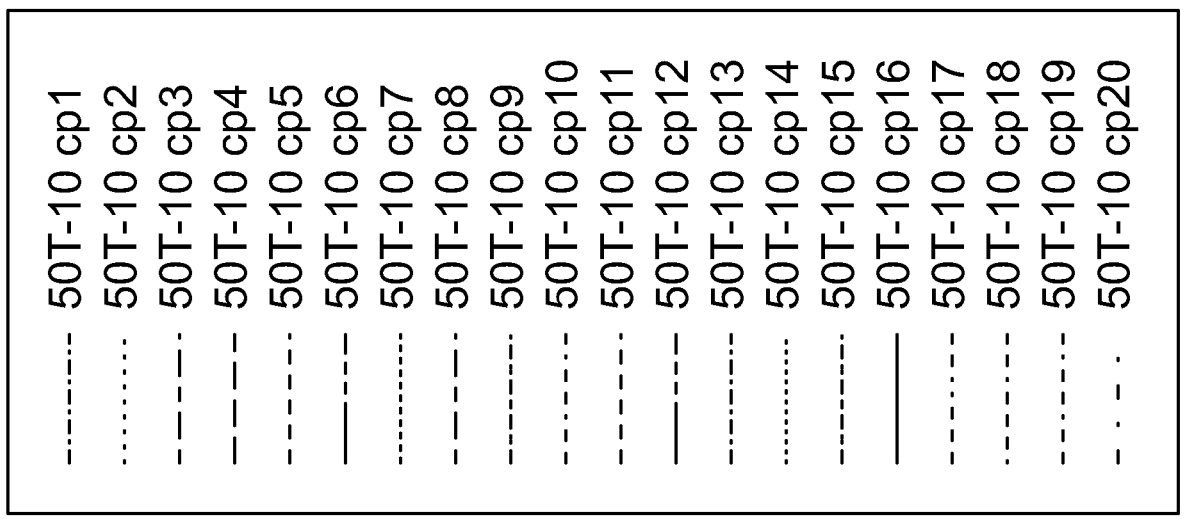
FIG. 5 shows the results of a GAS NEAR assay performed to determine the lowest copy number at which the assay could reproducibly detect target nucleic acid (requirement of detecting 95% of replicates). Shown are the results from the 50T mix when tested at 25° C. without a pre-heating step.
Figure 5:
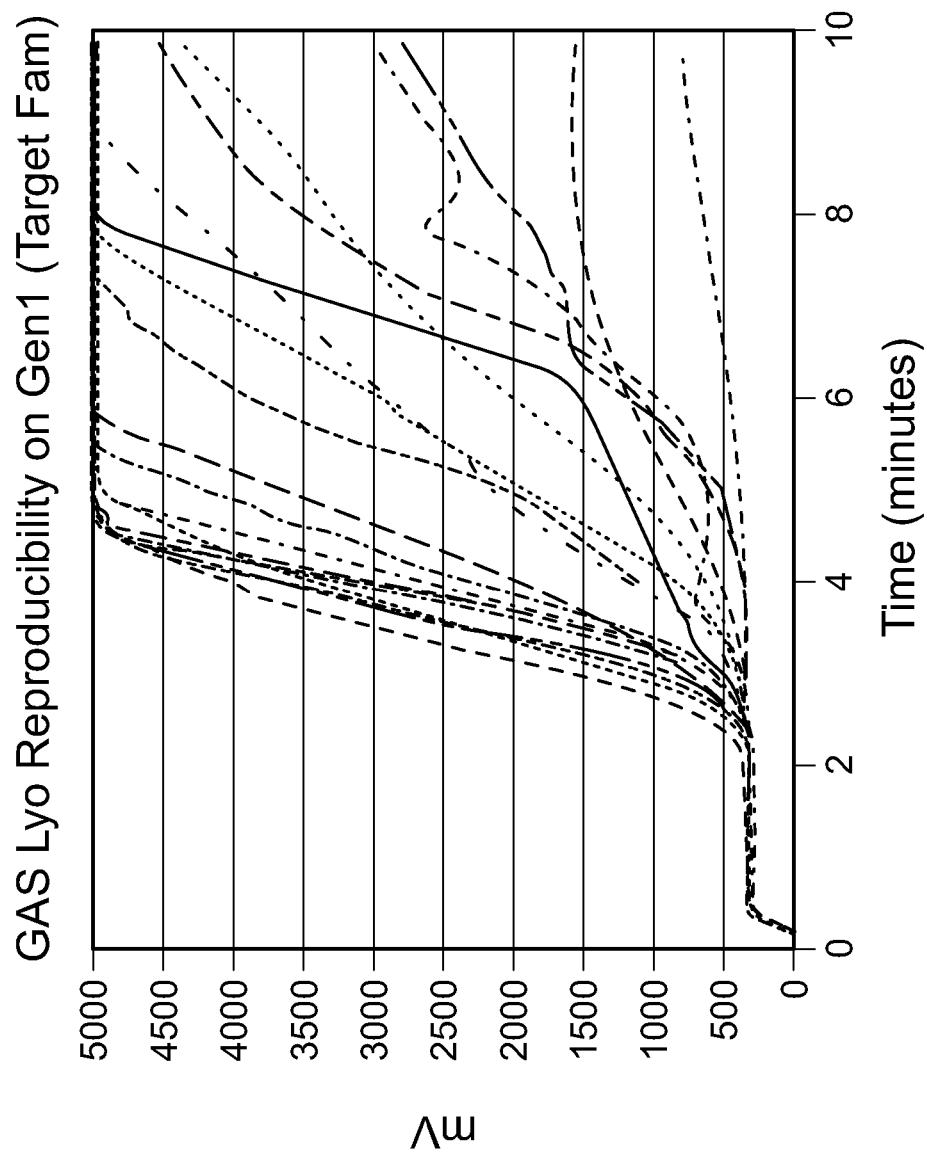
Figure 5:
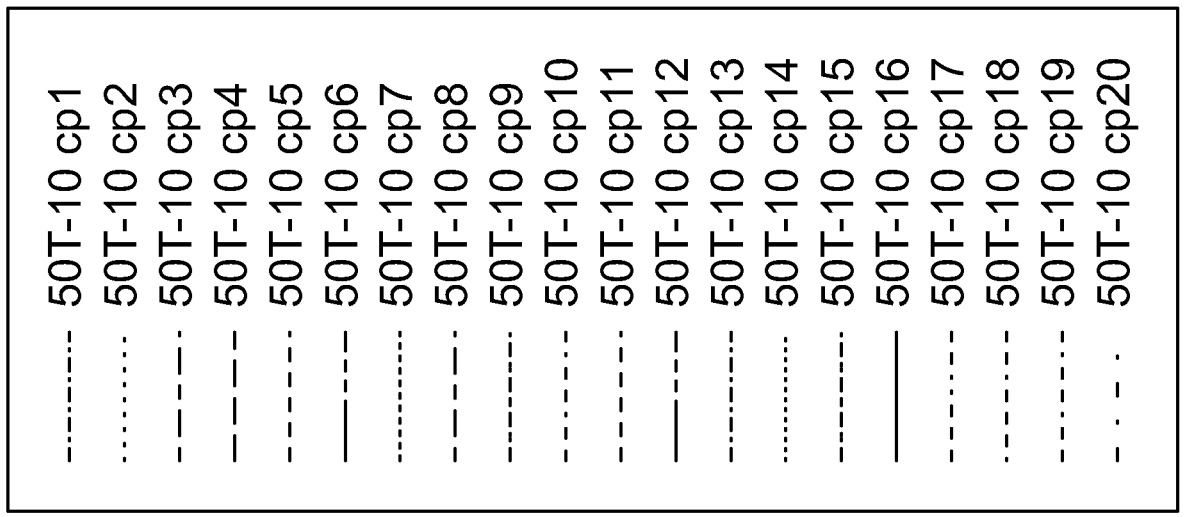
Figure 5:
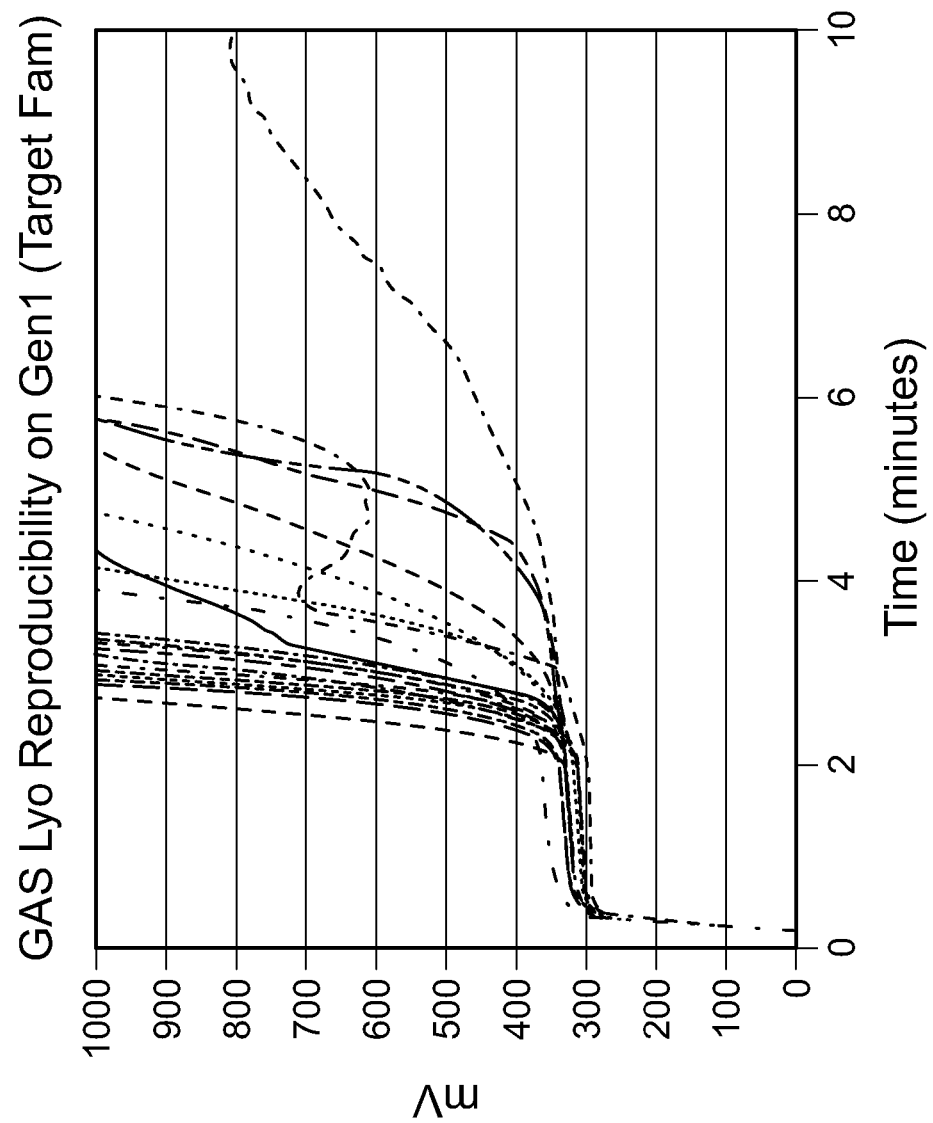

LOD and Reproducibility Using Inactivated GAS Organisms:

To determine the LOD of the GAS assay (50T, target only assay) and ensure its reproducibility, an experiment was performed to determine at which copy number the assay could detect 95% of the samples tested when twenty replicates were screened. The study was performed on the Alere i using inactivated GAS organisms (iGAS) at 25° C. with a 0 minute elution buffer pre-heat step. The results are shown in FIG. 5 and indicate that the 50T mix can readily detect 10 copies of iGAS even when the sample and lyophilized material are not heated prior to combining. The data show that 20/20 replicates were detected, although the fluorescence curves did differ in both speed and intensity.

Impact of Human Genomic DNA (gDNA) on GAS Assay.

Figure 6:
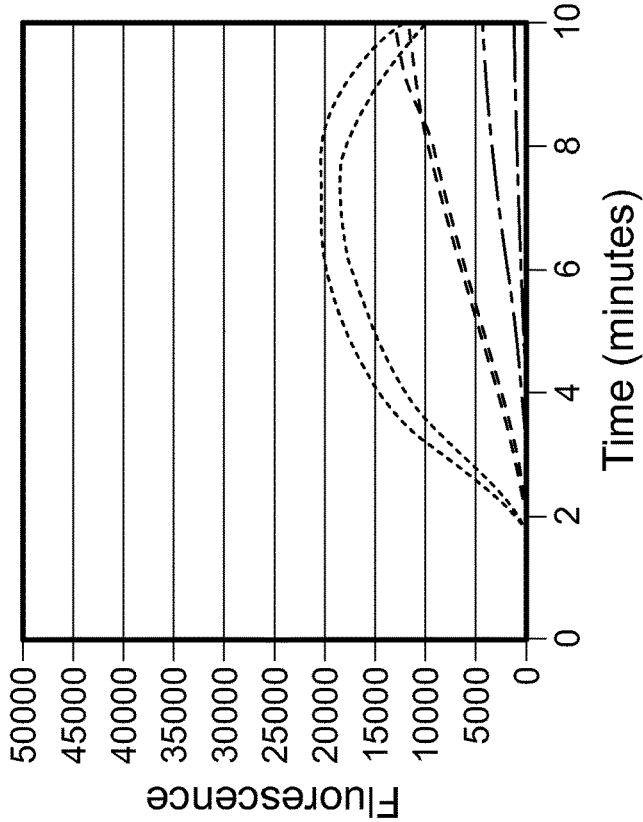
FIG. 6 shows the impact of human gDNA on the GAS assay. Lyophilized GAS NEAR assays were performed with 0, 25, 250 or 1,000 copies of target GAS gDNA in the presence of increasing amounts of background human gDNA (0 to 1,000 ng). Mixes 50I (0 copies of target; lower right panel) and 50T (25 copies (upper left panel), 250 copies (upper right panel) or 1,000 copies (lower left panel) of target gDNA) were screened on the Stratagene Mx3005P instrument using a typical hot start approach.
Figure 6:
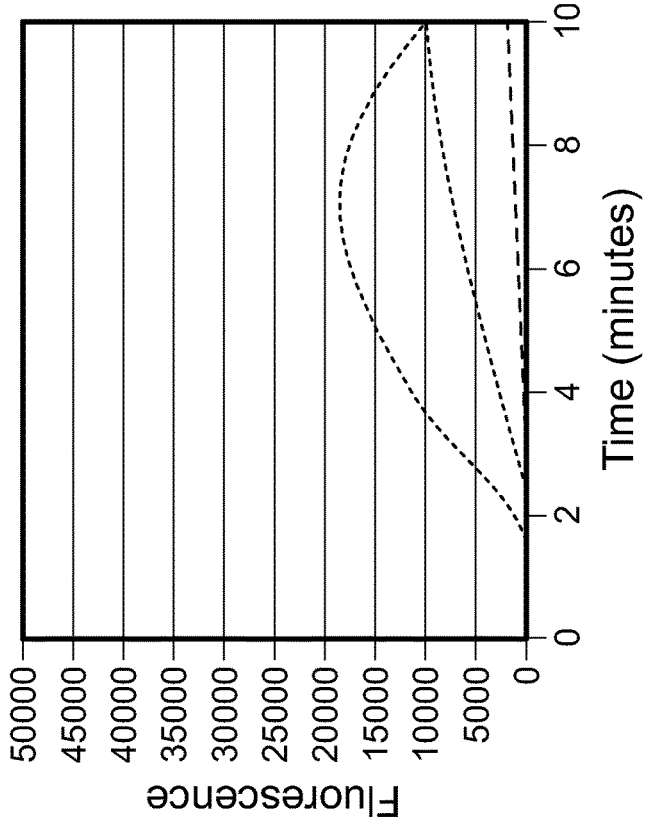
Figure 6:
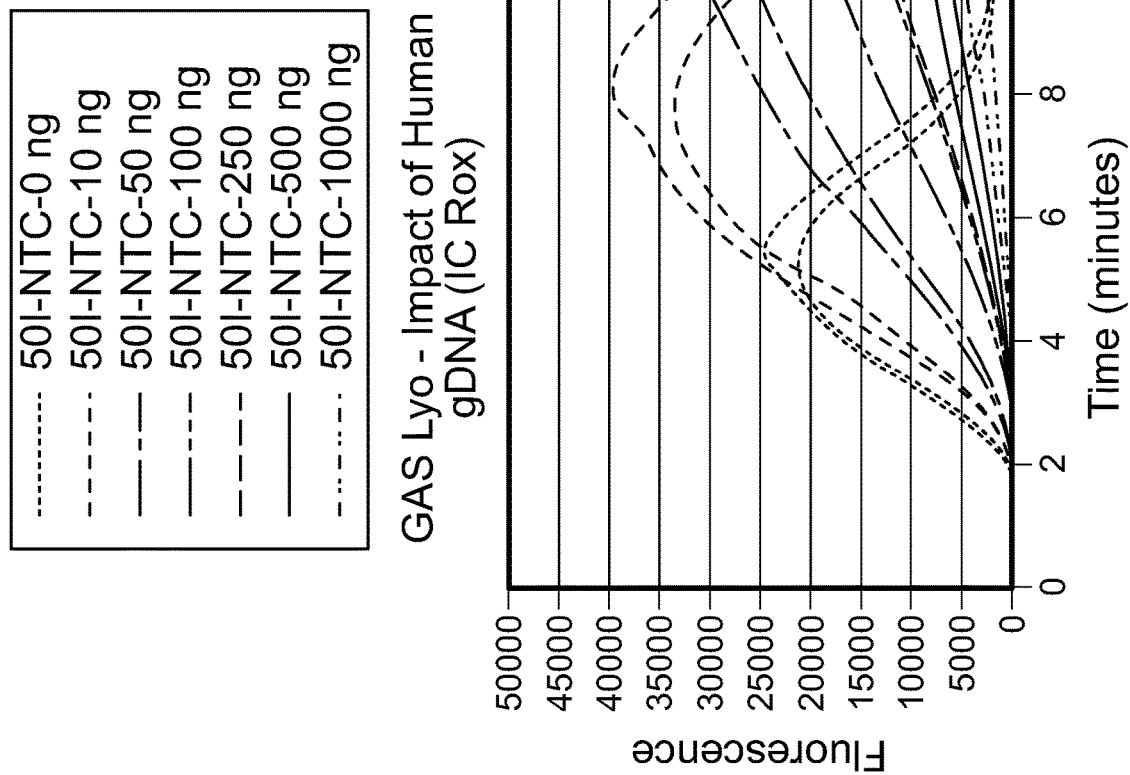
Figure 6:
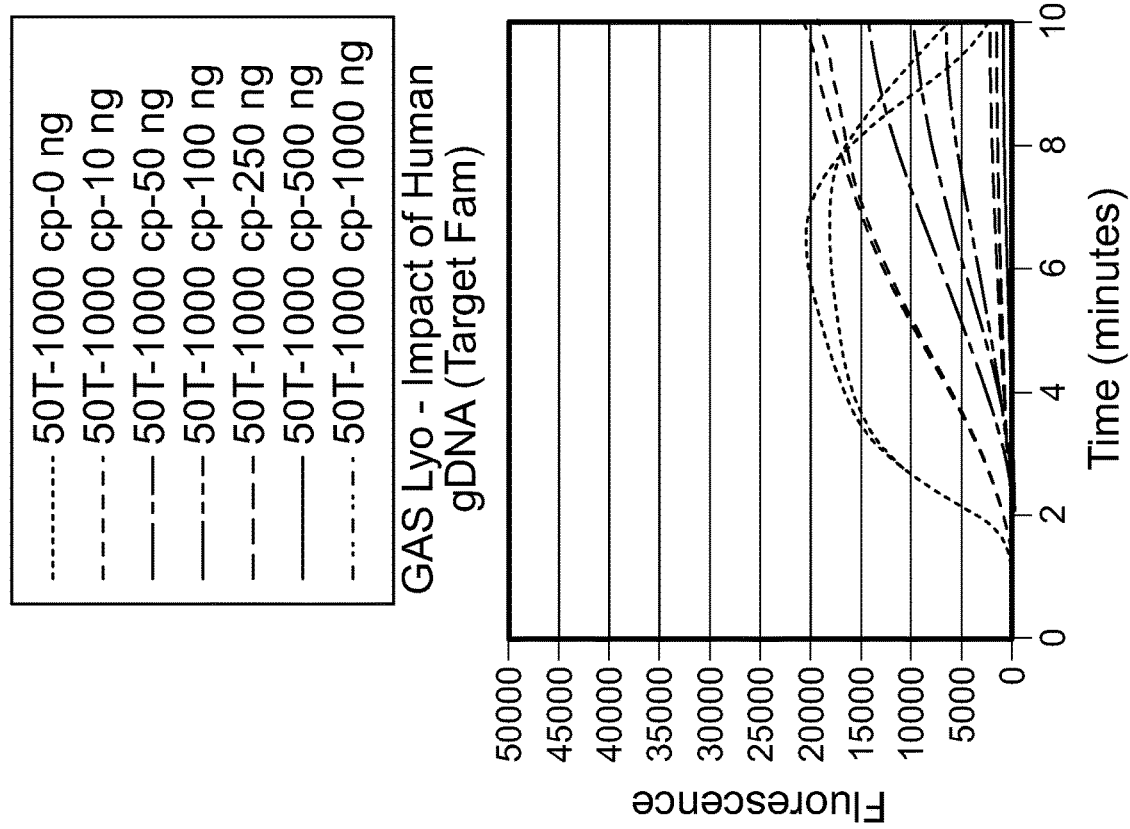

One potential inhibitor of the NEAR technology is human gDNA. When a throat swab sample is collected from a patient symptomatic for GAS infection, it is possible that human gDNA is also collected on the swab (from immune cells such as white blood cells or from local epithelial cells). In order to assess the impact that human gDNA has on the GAS assay, a study was performed using three different levels of GAS gDNA (25, 250 and 1000 copies) in the presence of 0, 10, 50, 100, 250, 500 or 1000 ng of human gDNA. As shown in FIG. 6, the presence of human gDNA does have an impact on GAS assay performance, and the impact is GAS target concentration dependent. When there is a low copy number of target GAS present in the reaction, 10 ng of human gDNA or more significantly inhibits the assay. At 250 copies of GAS target, the impact of 10 ng of human gDNA is less, and at 1,000 copies of GAS target, the effect of 10 ng of human gDNA on the assay is significantly less. In fact, when 1,000 copies of target is present in the assay, up to 100 ng of human gDNA can be tolerated, albeit with a slower amplification speed and reduced fluorescence signal. Testing of the 50I (IC only) mix showed a more robust response to human gDNA. When the 50I mix was tested in the presence of 0 copies of target GAS and up to 1,000 ng of human gDNA, the assay still produced a clearly positive signal at 500 ng of human gDNA (even at 1,000 ng of human gDNA the fluorescence signal was still above background).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising:

i) a forward template comprising a nucleic acid sequence comprising a recognition region at the 3' end that is complementary to the 3' end of the *Streptococcus pyogenes* (*S. pyogenes*) cell envelope proteinase A (cepA) gene antisense strand; a nicking enzyme binding site and a nicking site upstream of said recognition region; and a stabilizing region upstream of said nicking site;

ii) a reverse template comprising a nucleotide sequence comprising a recognition region at the 3' end that is complementary to the 3' end of the *S. pyogenes* cepA gene sense strand; a nicking enzyme binding site and a nicking site upstream of said recognition region; and a stabilizing region upstream of said nicking site; and iii) a probe oligonucleotide comprising a nucleotide sequence having at least 80, 85, or 95% identity to SEQ ID NO: 3 (ACAAGTATGTGAGGAGAGGCCATACTTGT).

2. The composition of claim 1 further comprising a probe oligonucleotide comprising a sequence complementary to the *S. pyogenes* cell envelope proteinase A (cepA) nucleotide sequence.

3. The composition of claim 2 wherein said probe oligonucleotide comprising a sequence complementary to the *S. pyogenes* cell envelope proteinase A (cepA) nucleotide sequence is conjugated to a detectable label.

4. The composition of claim 3 wherein the detectable label is selected from the group consisting of a fluorophore, an enzyme, a quencher, an enzyme inhibitor, a radioactive label, a member of a binding pair, and a combination thereof.

5. The composition of claim 1 wherein the portion of the nucleic acid sequence that is complementary to the 3' end of the target antisense strand is 8-30 nucleotides in length.

6. The composition of claim 1 wherein the portion of the nucleic acid sequence that is complementary to the 3' end of the target sense strand is 8-30 nucleotides in length.

7. The composition of claim 1 further comprising one or more of; a) a DNA polymerase; b) one or more nicking enzymes; and c) dNTPs or a mixture of dNTPs and ddNTPs.

8. The composition of claim 7 wherein the DNA polymerase is selected from the group consisting of *Geobacillus bogazici* DNA polymerase, Bst (large fragment), and exo-DNA Polymerase.

9. The composition of claim 7 wherein the one or more nicking enzymes is/are selected from the group consisting of Nt.BspQI, Nb.BbvCi, Nb.BsmI, Nb.BsrDI, Nb.BtsI, Nt.AlwI, Nt.BbvCI, Nt.BstNBI, Nt.CviPII, Nb.Bpu10I, Nt.Bpu10I, and N.BspD61.

10. The composition of claim 1 further comprising a lytic agent.

11. The composition of claim 10 wherein the lytic agent comprises a bacteriophage lysin.

12. The composition of claim 11 wherein the bacteriophage lysin comprises streptococcal C1 bacteriophase lysin (PlyC).

13. The composition of claim 1 wherein the composition is lyophilized.

14. The composition of claim 1 wherein the forward template and/or the reverse template comprises one or more modified nucleotides, spacers, or blocking groups.

15. The composition of claim 14 wherein at least one modified nucleotide includes a 2' modification.

16. The composition of claim 15 wherein at least one modified nucleotide includes a 2'-O-methyl.

17. The composition of claim 14 wherein the forward template and/or the reverse template comprises at least one phosphorothioate.

18. A kit comprising:

i) a forward template comprising a nucleic acid sequence comprising a recognition region at the 3' end that is complementary to the 3' end of the *Streptococcus pyogenes* (*S. pyogenes*) cell envelope proteinase A (cepA) gene antisense strand; a nicking enzyme binding site and a nicking site upstream of said recognition region; and a stabilizing region upstream of said nicking site;

ii) a reverse template comprising a nucleotide sequence comprising a recognition region at the 3' end that is complementary to the 3' end of the *S. pyogenes* cepA gene sense strand; a nicking enzyme binding site and a nicking site upstream of said recognition region; and a stabilizing region upstream of said nicking site; and iii) a probe oligonucleotide comprising a nucleotide sequence having at least 80, 85, or 95% identity to SEQ ID NO: 3 (ACAAGTATGTGAGGAGAGGCCATACTTGT).

19. The kit of claim 18 further comprising a swab.

20. The kit of claim 18 further comprising a lytic agent and one or more of; 1) dNTPs; or 2) a mixture of dNTPs and ddNTPs.

21. The kit of claim 18 optionally comprising reagent for extracting and/or isolating nucleic acid from a biological sample.

22. The kit of claim 18 wherein the template oligonucleotide comprises one or more modified nucleotides, spacers, or blocking groups.

23. The kit of claim 22 wherein at least one modified nucleotide includes a 2' modification.

24. The kit of claim 23 wherein at least one modified nucleotide includes a 2'-O-methyl.

25. The kit of claim 18 further comprising a polymerase.

* * * * *

UNITED STATES PATENT AND TRADEMARK OFFICE
CERTIFICATE OF CORRECTION

| | | |
|---|---|---|
| PATENT NO. | : 11,186,864 B2 | Page 1 of 1 |
| APPLICATION NO. | : 16/417071 | |
| DATED | : November 30, 2021 | |
| INVENTOR(S) | : Shen et al. | |

It is certified that error appears in the above-identified patent and that said Letters Patent is hereby corrected as shown below:

In the Claims

Claim 8, Column 27, Line 32 reads:
"bogazici DNA polymerase, Bst (large fragment), and exo-"
Whereas it should read:
"*bogazici* DNA polymerase, Bst (large fragment), and exo⁻"

Signed and Sealed this
Eighth Day of March, 2022

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 10

<210> SEQ ID NO 1
<211> LENGTH: 33
<212> TYPE: DNA
<213> ORGANISM: Artificial Sequence
<220> FEATURE:
<223> OTHER INFORMATION: oligonucleotide to detect Streptococcus
      pyogenes

<400> SEQUENCE: 1
agactccata tggagtctag ccaaacagga aca                                  33

<210> SEQ ID NO 2
<211> LENGTH: 33
<212> TYPE: DNA
<213> ORGANISM: Artificial Sequence
<220> FEATURE:
<223> OTHER INFORMATION: oligonucleotide to detect Streptococcus
      pyogenes

<400> SEQUENCE: 2
cgactccata tggagtcgaa agcaatctga gga                                  33

<210> SEQ ID NO 3
<211> LENGTH: 29
<212> TYPE: DNA
<213> ORGANISM: Artificial Sequence
<220> FEATURE:
<223> OTHER INFORMATION: oligonucleotide to detect Streptococcus
      pyogenes

<400> SEQUENCE: 3
acaagtatgt gaggagaggc catacttgt                                       29

<210> SEQ ID NO 4
<211> LENGTH: 35
<212> TYPE: DNA
<213> ORGANISM: Artificial Sequence
<220> FEATURE:
<223> OTHER INFORMATION: Amplification product from Streptococcus
      pyogenes

<400> SEQUENCE: 4
caaacaggaa caagtatggc ctctcctcag attgc                                35

<210> SEQ ID NO 5
<211> LENGTH: 35
<212> TYPE: DNA
<213> ORGANISM: Artificial Sequence
<220> FEATURE:
<223> OTHER INFORMATION: Amplification product from Streptococcus
```

```
                               pyogenes

<400> SEQUENCE: 5
gcaatctgag gagaggccat acttgttcct gtttg                                  35

<210> SEQ ID NO 6
<211> LENGTH: 24
<212> TYPE: DNA
<213> ORGANISM: Artificial Sequence
<220> FEATURE:
<223> OTHER INFORMATION: oligonucleotide to detect Streptococcus
      pyogenes

<400> SEQUENCE: 6
tgtagctgac accaccaagc taca                                              24

<210> SEQ ID NO 7
<211> LENGTH: 43
<212> TYPE: DNA
<213> ORGANISM: Artificial Sequence
<220> FEATURE:
<223> OTHER INFORMATION: oligonucleotide to detect Streptococcus
      pyogenes

<400> SEQUENCE: 7
acaatctgag gagctgacac caccaagcta ctgttcctgt tta                         43

<210> SEQ ID NO 8
<211> LENGTH: 33
<212> TYPE: DNA
<213> ORGANISM: Artificial Sequence
<220> FEATURE:
<223> OTHER INFORMATION: oligonucleotide to detect Streptococcus
      pyogenes

<400> SEQUENCE: 8
agactccaca cggagtctag ccaaacagga aca                                    33

<210> SEQ ID NO 9
<211> LENGTH: 33
<212> TYPE: DNA
<213> ORGANISM: Artificial Sequence
<220> FEATURE:
<223> OTHER INFORMATION: oligonucleotide to detect Streptococcus
      pyogenes

<400> SEQUENCE: 9
ggactccaca cggagtccgc cagcaatcug agg                                    33

<210> SEQ ID NO 10
<211> LENGTH: 44
<212> TYPE: DNA
<213> ORGANISM: Artificial Sequence
<220> FEATURE:
<223> OTHER INFORMATION: oligonucleotide to detect Streptococcus
      pyogenes

<400> SEQUENCE: 10
gcaatctgag gagctgacac caccaagcta ctgttcctgt ttga                        44
```